(12) United States Patent
Lior et al.

(10) Patent No.: US 8,740,768 B2
(45) Date of Patent: Jun. 3, 2014

(54) APPARATUS AND METHODS FOR CORRECTIVE GUIDANCE OF EATING BEHAVIOR AFTER WEIGHT LOSS SURGERY

(76) Inventors: Fleischer Lior, Katzir (IL); Tavori Isaac, Hertzeliya (IL)

(*) Notice: Subject to any disclaimer, the term of this patent is extended or adjusted under 35 U.S.C. 154(b) by 521 days.

(21) Appl. No.: 12/954,944

(22) Filed: Nov. 29, 2010

(65) Prior Publication Data

US 2011/0130625 A1    Jun. 2, 2011

Related U.S. Application Data

(60) Provisional application No. 61/264,787, filed on Nov. 28, 2009, provisional application No. 61/417,228, filed on Nov. 25, 2010.

(51) Int. Cl.
*A61F 2/00* (2006.01)

(52) U.S. Cl.
USPC ............................................................ 600/37

(58) Field of Classification Search
USPC .................. 600/29–31, 37; 606/139–158
See application file for complete search history.

(56) References Cited

U.S. PATENT DOCUMENTS

2008/0250340 A1*   10/2008   Dlugos et al. ............... 715/771

* cited by examiner

*Primary Examiner* — Charles A Marmor, II
*Assistant Examiner* — Catherine E Burk
(74) *Attorney, Agent, or Firm* — Fleit Gibbons Gutman Bongini & Bianco PL; Marty Fleit; Paul D. Bianco

(57) ABSTRACT

Apparatuses and methods for corrective guidance of eating behavior of a patient equipped with a gastric restriction device. The apparatus provides continuous monitoring or one or more parameters related to food passing through the gastric restriction device. Each monitored parameter is processed to provide a visual indication of the current eating behavior. The visual indication is used as input to the patient or a caregiver to modify the eating behavior. In some embodiments, the apparatus includes an emergency relief mechanism that automatically relieves excess pressure developing in the gastric restriction device. In some embodiments, the apparatus is enabled to deliver an appetite suppressant to modify the eating behavior.

27 Claims, 30 Drawing Sheets

APPARATUS AND METHODS FOR CORRECTIVE GUIDANCE OF EATING BEHAVIOR AFTER WEIGHT LOSS SURGERY

CROSS REFERENCE TO EXISTING APPLICATIONS

This application claims priority from U.S. Provisional Patent Application No. 61/264,787 filed 28 Nov. 2009 which is incorporated herein by reference in its entirety and from U.S. Provisional Patent Application No. 61/417,228 filed on 25 Nov. 2010 which is incorporated herein by reference in its entirety.

FIELD OF THE INVENTION

The invention relates in general to systems and methods for monitoring human eating patterns and for training and modifying such patterns, in particular after weight loss surgery. Furthermore, the present invention provides apparatus and methods for corrective guidance of eating behavior after weight loss surgery.

Yet more, the present invention provides device and method for monitoring, data collection, interpretation of eating behavior patterns, for training and eating behavior modification after weight loss surgery.

BACKGROUND OF THE INVENTION

Morbid obesity is a chronic condition. Gastric limiting techniques (e.g. "adjustable gastric banding" or AGB) are employed by surgeons to treat morbidly obese people who cannot lose weight by traditional means. In AGB, a gastric "band" made of an elastomer is placed around the stomach near its upper end. This creates a small pouch with a narrow passage into the rest of the stomach ("stoma orifice"), thus limiting the amount of food intake ("eating") by creating a feeling of fullness or uneasiness and by usually extending the time frame required to empty the pouch into the rest of the stomach. To control the size of the stoma orifice, the gastric band can be pressurized or depressurized by a physician. As a non-limiting example, the pouch is usually of a size of 50 cc to 5 cc, preferably 20 cc to 8 cc, and more preferably of about 15 cc. The stoma size can be increased or decreased with a saline solution by using a needle and syringe to access a small access port placed under the skin. The stoma orifice is governed by the amount of stomach tissue inside the band at the banding site. A desired passage size is about 12 mm in internal diameter.

The aim of restricting passage of food and liquids is to force the patient to change his/her eating behavior and thereby to induce a significant amount of weight loss. Researchers have demonstrated that the initial weight loss results after AGB are less predictable then those after gastric bypass. Patients after surgery are advised to chew their food thoroughly, eat slowly, take small bites, avoid certain foods, etc. Often, a large number of these patients do not adopt the required behavior and instead, eat forcefully, vomit, and intermittently suffer stoma occlusion events. These may result eventually in such complications as pouch enlargement, band erosion, reflux, and esophageal enlargement. In some cases, additional surgical interventions may be required.

The observation of gastric band action and the adjusting of stoma orifice by inflation/deflation are facilitated by X-ray imaging. A physician or technician acts to adjust (increase or decrease) the volume of fluid in the band based on inputs from the X-ray imaging. The volume decrease is done by removing an amount of fluid from the band via the external access port and fill line. Alternatively, components for adjusting the size of the gastric band may be implanted within the patient and, when a physical parameter such as intra-band pressure related to the patient food passage is determined, an external control unit outside the patient's body may be operated to power the implanted components to adjust the size of the band.

Monitoring the activity of the pouch created between the lower esophagus sphincter and the gastric band may generate important information related to the eating behavior of patients. Physiological parameters obtained by such monitoring may be useful to help a patient control his/her obesity, manage his/her diabetes, and monitor his/her gastro-esophageal reflux disease and the like.

Adjustable gastric restriction devices with sensors and actuators which enable control of the stoma orifice are disclosed for example in US patent applications No. 20070156013 by Birk and 20060173238 by Starkebaum. Birk discloses a self-regulating gastric band with pressure data processing, relates to a band adjustment assembly which is provided for implanting with the gastric band that includes a sensor for sensing fluid pressure in the expandable portion. The band adjustment assembly further includes a pump assembly connected to the expandable portion and to a controller that can operate the pump assembly to adjust the volume of the fluid in the band based on the sensed fluid pressure. Starkebaum's invention relates to a dynamically controlled gastric occlusion device that monitors at least one physiological parameter that varies as a function of food intake and controls the degree of gastric constriction of an occluding device, such as a gastric band, based on the monitored physiological parameter. In an embodiment, the dynamically-controlled gastric occlusion device controls the degree of gastric constriction based on time. The occluding device is dynamically opened or closed to either permit or prevent the passage of food through the gastrointestinal (GI) tract.

U.S. Pat. No. 5,724,025 to Tavori discloses a portable vital signs monitor in communication with a plurality of sensors capable of implantation, with two way communication, also allowing current diagnosis of a live body, possible reasons for abnormal diagnosis, based on physical data, anticipated behavior of the body and monitoring physical changes resulting from actual treatment.

A large number of studies have determined the following:
1) Pouch volume and stoma size are important determinants for the success of AGB.
2) Proper stoma adjustment can effect immediate and late results of the AGB and reduce complications such as Spherical Pouch Dilatation (SPD).
3) Fast eating or improper chewing of the food can lead to excessive pouch enlargement and impaired surgical results.
4) Adoption of favorable eating behavior is imperative for long term success of the AGB
5) Adoption of mal-eating behaviors can reduce the success rate of AGB.

Although gastric bands can limit food intake, it is worth recognizing that eating is a form of behavior that can be defined according to its structure (frequency duration and size of eating episodes). This pattern of behavior can be further analyzed at the level of a single meal, where the same structure (frequency duration and size of eating episodes—bites) rules and defines the meal size. In principle, this behavior operates through the skeletal musculature and is subject to conscious control. Therefore, people should be able to volitionally decide when and how to control their own eating. In practice, people find it extremely difficult to exert control and many obese people claim that their eating is out of (their) control.

AGB or other bariatric procedures such as: Gastric-By-Pass, Sleeve Gastrectomy, Vertical Banded Gastroplasty and Duodenal Switch, these procedures are not known to provide a patient with visual data or information regarding his/her eating behavior pattern, yet the patient is expected to adopt different eating behavior with respect to frequency, duration or size of bite or meal. The realization and visualization of eating behavior patterns is required to the patient in order to induce conscious and correct eating behavior modification. Therefore there is a need for a tool that will provide the AGB and other bariatric procedures obese patients a guided and controlled eating monitoring system and/or "pacer" that will enable them to learn and gain a new control over their eating behavior.

Out of the clinical literature from the last 15 years and over 500,000 patients with AGB it is clear that it is very difficult to obtain hard quantitative data on the true food intake behavior of AGB or other bariatric procedures obese patients. It is clear that in some AGB obese individuals, habitual food intake or its caloric value are greater than it is normally assumed to be and is often erratic and apparently unregulated. In order for health care givers to be able to advice and guide those patients to better regulate eating habits and behavior, there is clearly a need for a method and apparatus that will enable them to monitor and obtain objectively recorded eating behavior patterns. It would also be advantageous to have systems and methods to improve the action of AGB or other patients post bariatric procedures by automatically releasing excessive pressure buildups.

SUMMARY OF THE INVENTION

The invention provides, in various embodiments, devices, apparatuses and methods for gastric restriction and data collection, interpretation of eating behavior patterns and for training and eating behavior modification after any type of weight loss surgery. In some embodiments, implanted sensors attached to a gastric band or extra corporal sensors sense, during a meal, at least one parameter like viscosity, density or quantity of a bolus (dose) of food or substance passing through the stoma, the time of the passage of a bolus, intervals between boluses, duration of a meal, pressure exerted by the food bolus passage or substance and/or macronutrient contents passing through the pouch and the stoma orifice produced by a restriction device. Each sensed parameter may be processed into an indication of the caloric value of the meal.

In some embodiments there is provided an apparatus and method for monitoring food passage through a gastric band stoma and for monitoring eating patterns and behavior by providing the patient real time realization or visualization of his/her eating behavior as compared to a desired behavior. The data collected may be downloaded into a computer system that will chart the eating events and provide the patient, the surgeon/dietician information regarding the following:

Frequency of eating events during the day.
Number and size of meals.
Consistency of the consumed food (liquid, semi-liquid or solid).
Eating behavior data such as: speed of eating, quality of chewing, drinking during the meal, binge eating, night eating, vomiting.
Accurate adjustment to an "ideal stoma size".
Compliance.
Eating behavior improvement.
Eating behavior adoption and assimilation.
Indication of the presence or development of a complication.
Advise patient to "stop eating" based on volume of food consumed or caloric intake.

In some embodiments there is provided an apparatus and method for triggering up coming food substance before monitoring food passage through a gastric band stoma and for monitoring eating patterns and behavior by sensing hand motion. Sensed element is incorporated to the system microcontroller, or microprocessor, downloaded with other data using communication port, and provides a flag to the system for a certain time constant to pass before food passage through gastric band is sensed.

In some embodiments, at least one sensed parameter is used to provide a command to an emergency relief valve attached to the gastric band to release pressure buildup, an action performed in prior art only manually by a physician in an emergency room.

In some embodiments, at least one sensed parameter is used to provide corrective guidance for the patient, who, with the benefit of the band's repetitive feedback capability, can adjust and change his/her eating behavior and the present perception of the body signals of hunger and satiety. This is particularly important since satiety is considered by the medical literature to be a conditioned reflex, and eating behavior is considered an acquired behavior. The patient and/or a physician or caregiver is provided with objective behavioral data regarding the patient's eating behavior. The data is used to assist the patient to adopt positive and favorable eating behaviors.

In some embodiments, at least one sensed parameters used to provide the physician or patient processed data and notes for further additional lookups or investigations.

In some embodiments, at least one sensed parameter is converted into an instruction to the patient to activate an infusion pump to deliver a dose of a satiety inducing substance. The instruction generated will depend on a preset caloric level the patient is allowed to consume in that meal.

In some embodiments, at least one sensed parameter is converted into an instruction to the patient to activate an infusion pump to deliver a dose of a satiety inducing substance. The instruction generated will depend on a preset caloric level the patient is allowed to consume in that meal.

Thus, it is one object of the present invention to provide a method for modifying the eating behavior of a patient equipped with a gastric restriction apparatus (GRA), comprising the steps of:
a) monitoring a parameter related to food currently passing through the GRA;
b) processing said parameter, thereby providing an indication of a current eating pattern; and
c) increasing the signal to noise ratio so as to gather food passage events;
d) generating an eating behavior pattern descriptive report;
wherein said step of generating an eating behavior pattern descriptive report additionally comprising step of analyzing at least one parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to provide the method as defined above, wherein said step (d) generating is assisted by at least one external sensor; further wherein said at least one external sensor is selected from a group consisting of a vertical position sensor, thermometer, thermal sensor, force transducer, or a strain gauge, weighing, oscillating sensor for mass detection or any combination thereof.

It is another object of the present invention to provide the method as defined above, additionally comprising step of using the indication of said current eating pattern to modify the eating behavior of said patient.

It is another object of the present invention to provide the method as defined above, wherein said step of increasing the signal to noise ratio additionally comprising at least one step selected from (a) filtering the influence of esophagus & Lower esophagus sphincter (LES); (b) filtering the influence of patient posture while eating on food passage through the GRA; or any combination thereof.

It is another object of the present invention to provide the method as defined above, wherein said parameter is pressure; further wherein said step of processing said parameter is performed by indication selected from the group consisting of volumetric flow, mass flow and Reynolds number or any combination thereof.

It is another object of the present invention to provide the method as defined above, additionally comprising step of indicating said current eating behavior through a display to the patient.

It is another object of the present invention to provide the method as defined above, further comprising the step of calibrating the GRA to a desired restriction based on the monitored parameter.

It is another object of the present invention to provide the method as defined above, additionally comprising at least one step selected from (a) monitoring said parameter on a standard food substance to obtain at least one standard food parameter; (b) comparing said monitored parameter to the at least one standard food parameter; or any combination thereof.

It is another object of the present invention to provide the method as defined above, additionally comprising step of indicating said eating behavior pattern to at least one selected from a group consisting of (a) said patient; (b) predetermined physician; or any combination thereof.

It is another object of the present invention to provide the method as defined above, wherein said step of indicating is performed by at least one selected from a group consisting of (a) the patient; (b) said physician through appropriate instructions to the patient; or any combination thereof.

It is another object of the present invention to provide an apparatus for modifying the eating behavior of patient equipped with a gastric restriction apparatus (GRA) comprising:
  a) monitoring means for monitoring a parameter related to food currently passing through the GRA;
  b) an intra-corporal emergency relief mechanism;
  c) at least one external device adapted to indicate whether said measured parameter is an eating or drinking event; and,
  d) processing means adapted for increasing the signal to noise ratio so as to gather food passage events.

It is another object of the present invention to provide the apparatus as defined above, wherein said an intra-corporal emergency relief mechanism is adapted for automatically relieve of pressure development.

It is another object of the present invention to provide the apparatus as defined above, wherein said pressure is developed by food currently passing through the GRA.

It is another object of the present invention to provide the apparatus as defined above, wherein said at least one external device adapted to initiating the time collection component for improved eating behavior analysis and monitoring.

It is another object of the present invention to provide the apparatus as defined above, wherein said processing means are adapted to filter at least one selected from a group consisting of (a) the influence of the esophagus & LES; and (b) the influence of patient posture while eating on food passage through the GRA; (c) other noise to collect food passage events; or any combination thereof.

It is another object of the present invention to provide the apparatus as defined above, wherein eating behavior pattern descriptive report is provided based on the analysis of at least one parameter selected from a group consisting of constant speed eater, fast or accelerated speed eater, night eater, binge eater, total size of meal, average volume of meal, and average time of meal, volumetric consumption by time, shifting to liquid food consumption, vomiting events, type of food consumed, meal times during the day and duration, new adjustment validation data and short/long term change of pressure events as a result of new adjustment or any combination thereof.

It is another object of the present invention to provide the apparatus as defined above, wherein said parameter is pressure; further wherein the processing of said parameter is performed by indication selected from the group consisting of volumetric flow, mass flow and reynolds number or any combination thereof.

It is another object of the present invention to provide the apparatus as defined above, additionally comprising means adapted to indicate said current eating behavior through a display to the patient.

It is another object of the present invention to provide the apparatus as defined above, wherein said GRA is calibrated to a desired restriction based on the monitored parameter.

It is another object of the present invention to provide the apparatus as defined above, additionally comprising means adapted to indicate said eating behavior pattern to at least one selected from a group consisting of (a) said patient; (b) a predetermined physician; or any combination thereof.

It is another object of the present invention to provide the apparatus as defined above, wherein said external device is selected from a group consisting of a vertical position sensor, thermometer, thermal sensor, force transducer, or a strain gauge, weighing, oscillating sensor for mass detection or any combination thereof.

It is another object of the present invention to provide the apparatus as defined above, wherein said indication is performed by at least one selected from a group consisting of (a) the patient; (b) said physician through appropriate instructions to said patient.

It is another object of the present invention to provide a method for automatically releasing pressure developing in a gastric restriction apparatus (GRA), comprising the steps of:
  a) providing an intra-corporal emergency relief mechanism coupled to the GRA;
  b) monitoring pressure related to food currently passing through the GRA;
  c) using the emergency relief mechanism to automatically release pressure in the GRA when an excessive pressure is indicated by the monitoring; and, d) indicating whether said measured parameter is an eating or drinking event;

wherein said step (d) of indicating is performed by at least one gastric-external device.

It is still an object of the present invention to provide the method as defined above, wherein the GRA is used in addition to any bariatric procedure.

It is still an object of the present invention to provide the method as defined above, additionally comprising step of selecting said external device from a group consisting of a vertical position sensor, thermometer, thermal sensor, force transducer, or a strain gauge, weighing, oscillating sensor for mass detection or any combination thereof.

It is lastly an object of the present invention to provide the apparatus as defined above, implanted to a patient having any other bariatric procedure hence forming an apparatus for modifying eating behavior of a patient.

BRIEF DESCRIPTION OF THE DRAWINGS

The invention is herein described, by way of example only, with reference to the accompanying drawings, wherein.

DETAILED DESCRIPTION OF THE INVENTION

In the following description, where used, identical numbers in different figures refer to identical components.

Figure 1:
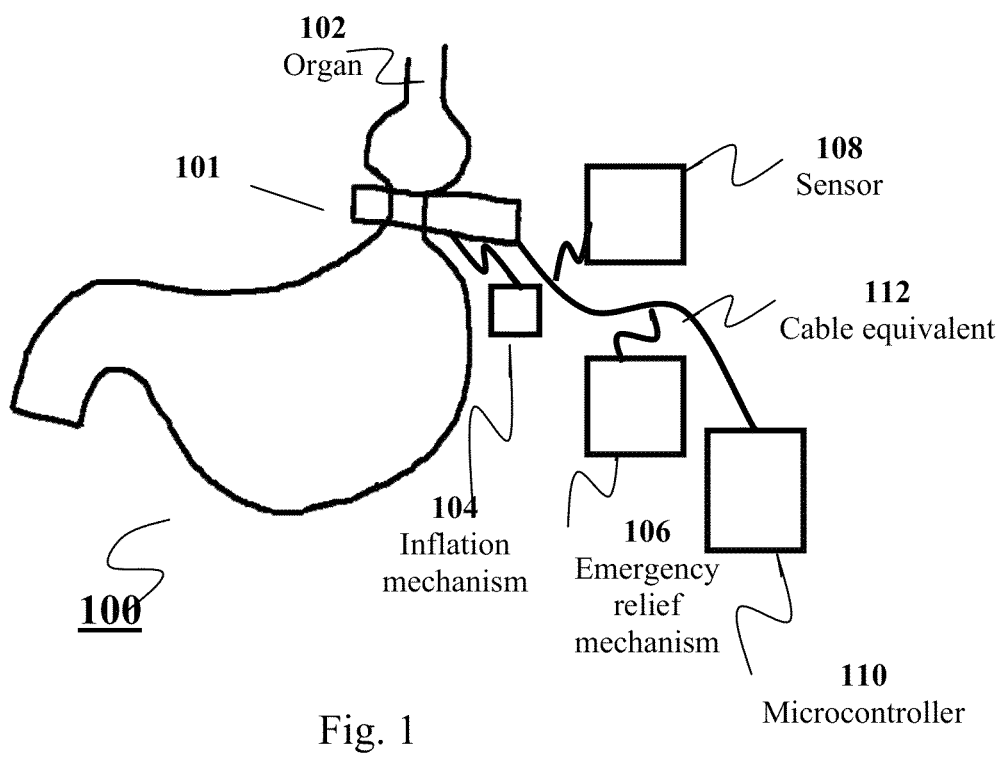
FIG. 1 shows an embodiment of an apparatus of the invention used in the stomach.

Returning now to the figures, FIG. 1 shows an embodiment of an apparatus (or "device") of the invention the form of an apparatus 100. Apparatus 100 is generally described as being implanted around an organ 102 in the alimentary, esophageal, stomach, intestine or colon tract. For ease of example, organ 102 is considered to be the stomach, apparatus 100 thereby being a gastric restriction apparatus (GRA). It is to be clearly understood that an apparatus of the invention may be used singly or plurality of such devices be implanted around an organ or in conjunction with any other bariatric procedure such as: Gastric-By-Pass, Sleeve Gastrectomy, Vertical Banded Gastroplasty and Duodenal Switch It is to be clearly understood that an apparatus of the invention may be implanted around other organs mentioned above, further including urinary tract or blood vessels, where its use will be based on the principles and actions described below. In common with known GRAs, apparatus 100 includes a gastric band 101, an inflation mechanism 104 operative to inflate the apparatus and bring it into intimate contact with organ 102, and at least one sensing element (sensor) 108. Inflation mechanisms useful for the purposes of the invention are known in the art, for example the balloon type vessel manufactured by Johnson & Johnson or by Allergan Corporation. Sensor 108 may be any sensor that can produce an output by sensing any physical phenomena, for example pressure, temperature, impedance, optical properties, ultrasonic properties and the like. A sensed parameter may be related to food intake in well-known ways. Such a parameter may be food viscosity, food density, food quantity, number of food boluses, bolus passage time, intervals between boluses, duration of a meal, pressure and/or macronutrient content. The description continues with reference to "a" (single) sensor, with the understanding that different sensors may be employed to provide different sensed parameters. In contrast with known GRAs, apparatus 100 further includes an emergency relief mechanism 106. Emergency relief mechanism 106 is operative to relieve the pressure inside the inflation mechanism without human intervention.

In some embodiments, apparatus 100 further includes a microcontroller (processor) 110 which communicates with sensor 108 and emergency relief mechanism 106. The communication may be two way, wired or wireless, in ways known in the art. If wired, the communication may be via a cable equivalent 112. A "cable equivalent" in this disclosure may refer to one or more electrical wires, optical or mechanical means, a hydraulic vessel or a pneumatic vessel, the latter two with or without a separating membrane which separates the sensor from the inner fluid of the gastric band. A hydraulic vessel cable equivalent can be used as an ultrasound (US) emitter/reflector of intra-band events. Microcontroller 110 may be used to activate, operate or read sensor 108. The data received from the sensor may be indicative of plug flow, tissue erosion, organ dilatation and the like. Microcontroller 110 is further capable of interpreting a sensed parameter and capable of supplying inputs or commands for eating behavior modification. Data processed by microcontroller 110 may be displayed to the patient and/or to a physician, stored, or transmitted to an external entity by well-known means. In some embodiments, microcontroller 110 is capable of pacing a meal, i.e. decide on the time to start, the time to swallow and the time to end the meal.

Figure 2A:
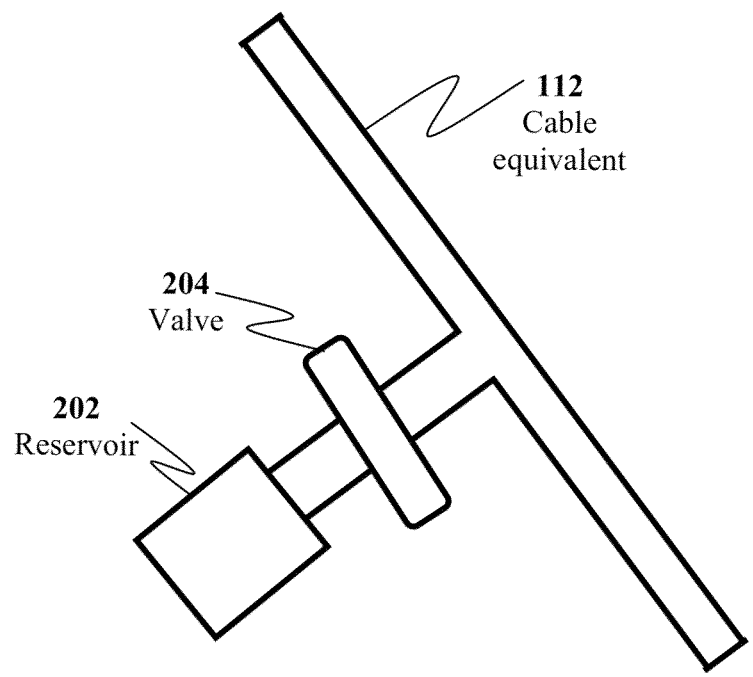
FIG. 2A shows details of one embodiment of an emergency relief mechanism.

FIG. 2A shows details of an embodiment of emergency relief mechanism in the form of a mechanism 106'. Mechanism 106' includes a reservoir 202 and a valve 204. Valve 204 couples reservoir 202 to cable equivalent 112. Reservoir 202 is dimensioned to receive a substantial portion of a calibrating saline solution, which is used to generate inflation in apparatus 100, hence relieving the stoma. Valve 204 may be a common spring loaded ball relief valve, a duckbill valve, a diaphragm valve and the like. Such valves are commonly available from Humphrey Kalamazoo, Mich. USA, operated mechanically, electromechanically or electronically, directly or by remote commands.

Figure 2B:
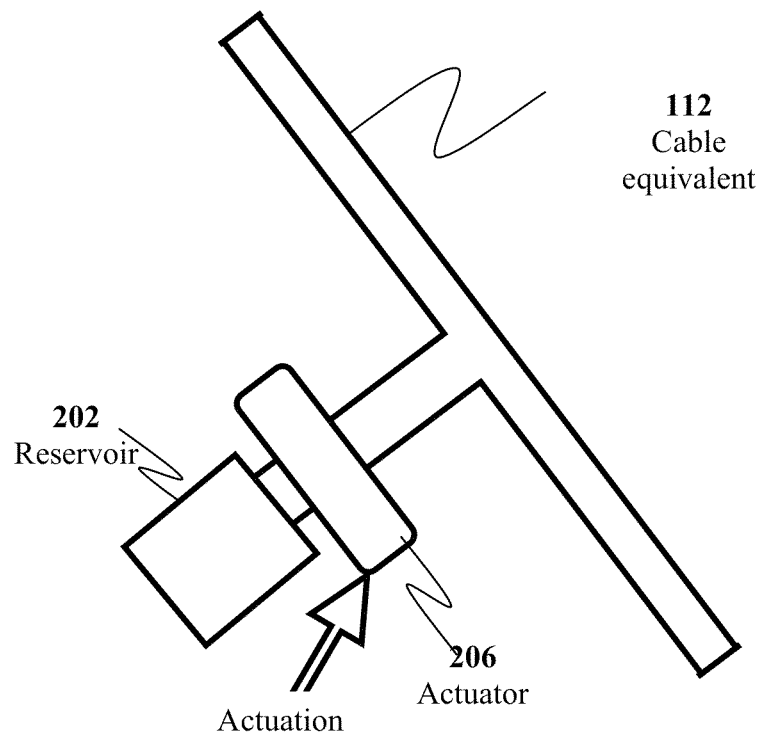
FIG. 2B shows details of another embodiment of an emergency relief mechanism.
Figure 12:
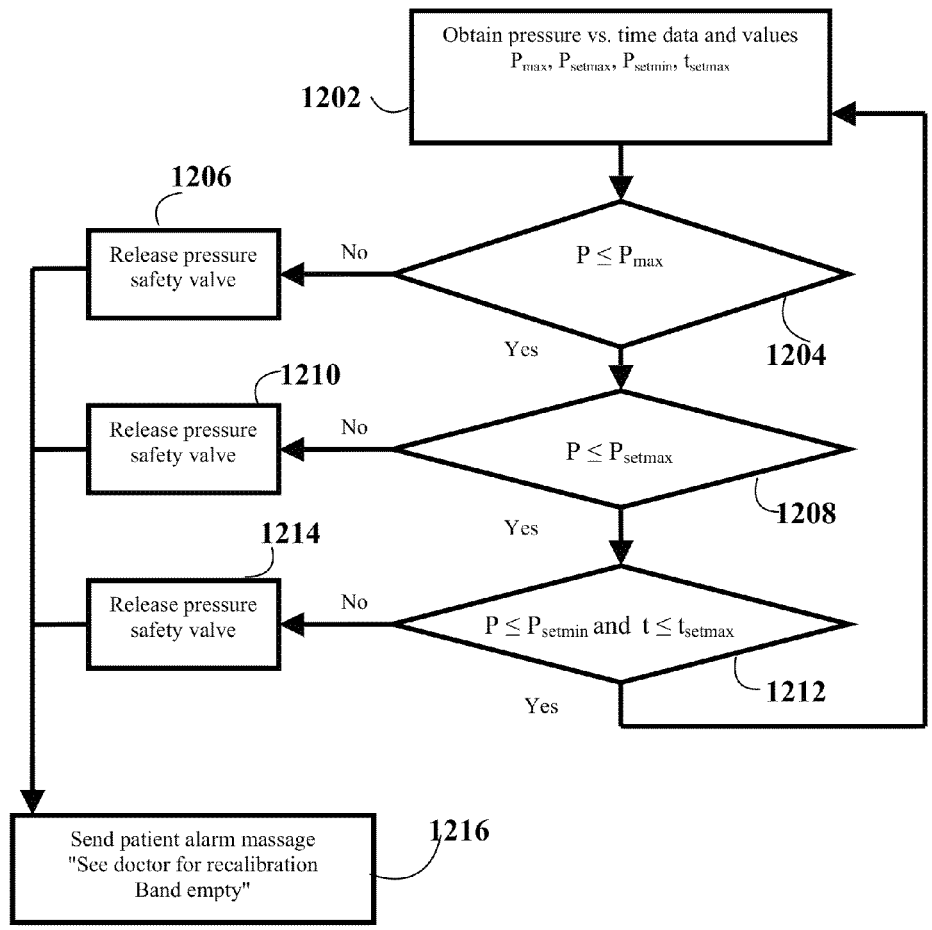
FIG. 12 describes a method of relieving pressure in the AGB using the relief emergency mechanism.

FIG. 2B shows details of another embodiment of emergency relief mechanism in the form of a mechanism 106". Mechanism 106" includes a common actuator 206 (instead of valve 204) capable of actuation and coupled to reservoir 202. Actuator 206 may be manually operated by the patient, e.g. by using extra-corporal push, magnetic, or telemetric systems, well known in the art. Another way to operate actuator 206 is by controls generated by processor 110, according to an operating algorithm described with reference to FIG. 12. Whether using valve 204 or actuator 206, when pressure reaches above a predetermined value (i.e. $P_{max}$) set in the factory, the relief valve discharges an excessive saline solution into reservoir 202. Alternatively, excessive saline may be discharged into the abdomen. In some embodiments, valve 204 and actuator 206 can be combined to work together. Sensor 108 senses both excessive pressure and pressure drop, and notifies microcontroller 110 of the pressure relief event. The patient is notified that device 100 is partially active, and is encouraged to visit a physician for monitoring and recalibration of the apparatus. The physician recalibrates device 100 using a standard procedure, empties the emergency relief mechanism by using a syringe (Huber needle) inserted in reservoir 202 and resets the emergency relief mechanism back to fully active status. The emergency relief mechanism is dimensioned such that it is visible during radiography and physically separable from a common calibration injection port or designed as an injection port.

Figure 3:
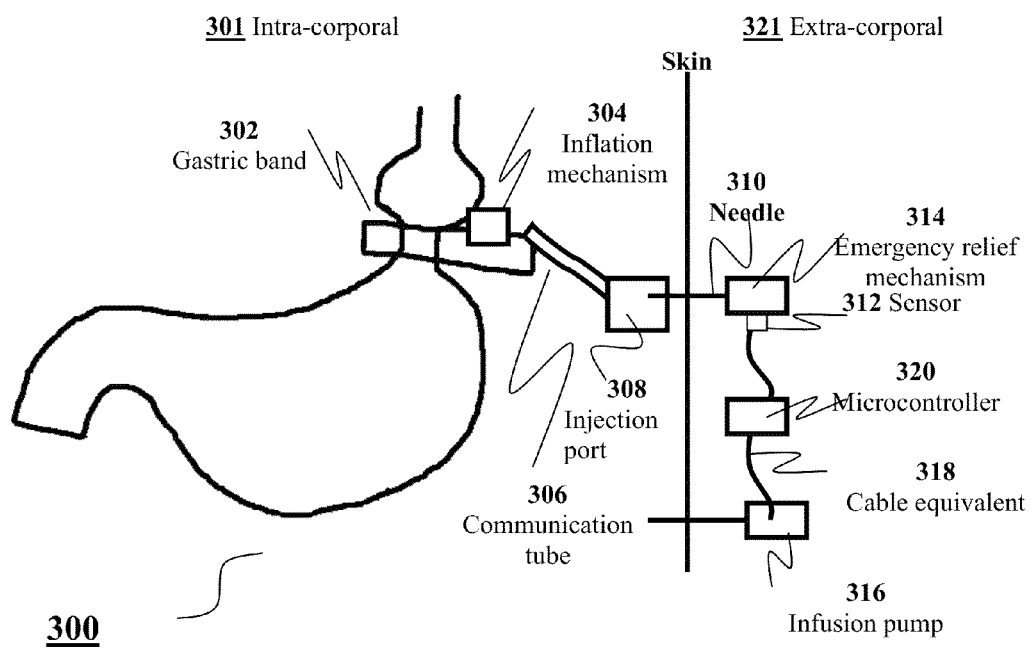
FIG. 3 shows another embodiment of an apparatus of the invention.

FIG. 3 shows an apparatus of the invention in the form of an apparatus 300. Apparatus 300 includes an intra-corporal section 301 and an extra-corporal section 321. Intra-corporal section 301 includes a gastric band 302 with an inflation mechanism 304, a communication tube 306 and a common injection port 308. Extra-corporal section 321 includes a needle 310 used to provide access into common injection port 308 and for inflation and deflation. The needle is coupled with a sensor 312 and with an emergency relief mechanism 314. Sensor 312 and an infusion pump 316 are connected via a cable equivalent 318 to a micro-controller 320. The pump can be activated automatically or manually. In some embodiments, the pump can control intra-muscular administration of a dose of a hunger controlling hormone. An exemplary such hormone is PYY36, a well known hunger controller.

Cable equivalent 318 is defined as a two way communication device, capable of uploading data, flags, triggering or other commands, or being downloaded with data, flags, triggering or other commands, and capable of interfacing external sensors. As a non limiting example, a flag created by a hand motion near the mouth. Such an arrangement allow for low electrical resource operation as the micro-controller 320 starts to operate when a flag is set.

Figure 4A:
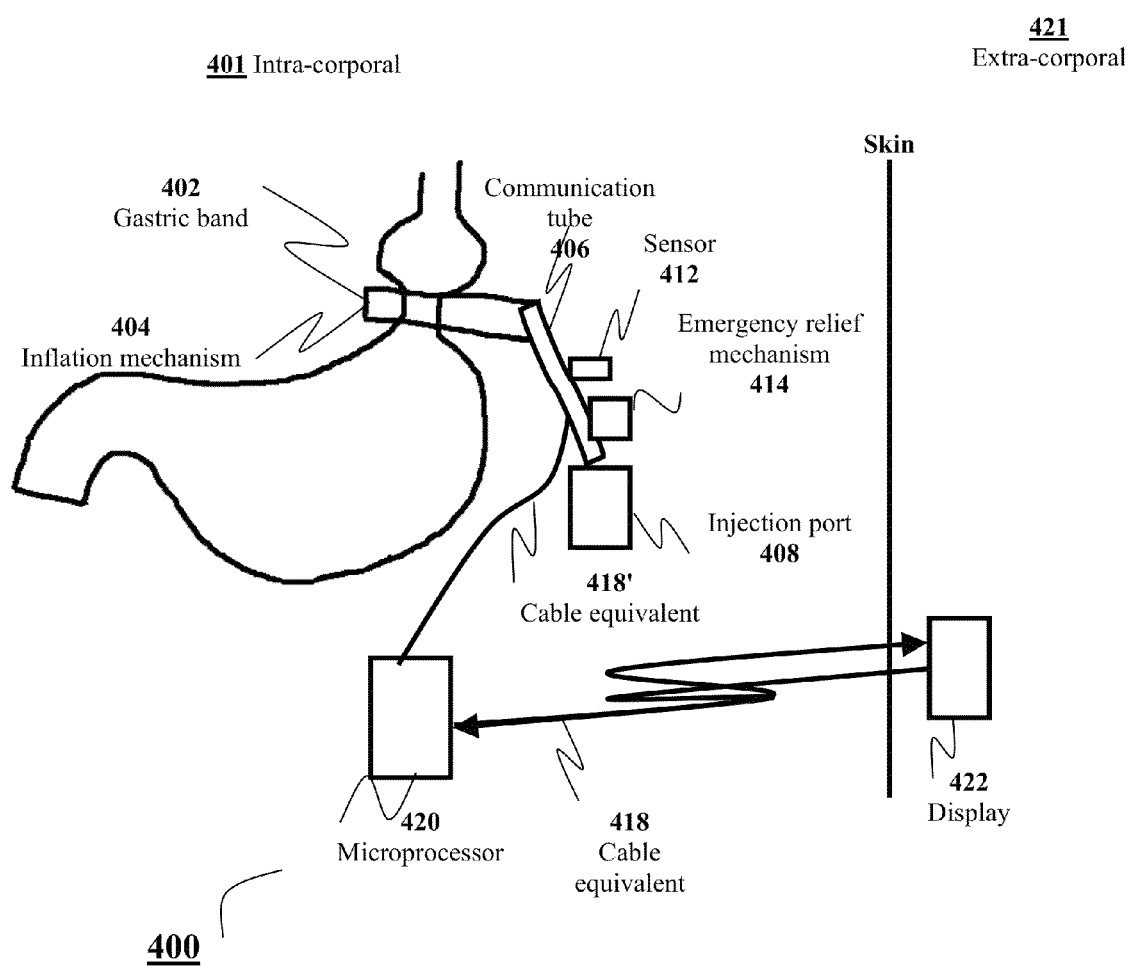
FIG. 4A shows yet another embodiment of an apparatus of the invention.

FIG. 4A shows another embodiment of an apparatus of the invention in the form of an apparatus 400. As with apparatus 300, apparatus 400 includes an intra-corporal section 401 and an extra-corporal section 421. Section 401 includes a gastric band 402 with an inflation mechanism 404, a communication tube (hydraulic line) 406 and a common injection port 408. In some embodiments, a sensor 412 and an emergency relief mechanism 414 may be connected via communication tube 406 in any position along communication tube 406. In some embodiments, sensor 412 and emergency relief mechanism 414 may be connected by a cable equivalent 418'. In some embodiments, sensor 412 and emergency relief mechanism 414 may be directly combined with gastric band 402 in a single unit. In some embodiments, sensor 412 and emergency relief mechanism 414 may be combined with a microcontroller 420 in a single unit and be in communication with gastric band 402 via a cable equivalent 418' and communication tube 406. Apparatus 400 may further include a display 422 for displaying to the patient indications related to eating behavior, eating behavior modifications and administration of substances. The displaying may be visual, tactile, auditory or sensory. Communication with microcontroller 420 is via cable equivalent 418. Cable equivalent 418 is defined as a two way communication device, operating with any available communication protocol, TCP/IP, bluetooth, RS 232, and the like capable of uploading data, flags, triggering or other commands, or being downloaded with data, flags, triggering or other commands, capable of interfacing with external sensors such as a vertical position sensor (which is adapted to provide, e.g., information as for the position of the patient; i.e., is the same is standing, lying down, bending, leaning et cetera), thermal sensor, oscillating sensor for mass detection and the like. As a non limiting example, a flag created by a hand motion near the mouth.

Such an arrangement allow for low electrical resource operation as the microcontroller 420 starts to operate when a flag is set Such a flag may be triggered using an external device, such as a hand eating motion detection and analysis device, a vertical position sensor, thermal sensor oscillating sensor for mass detection and the like. Such an external device, preferably mounted on the arm between the wrist and the elbow, in the shape of a bracelet, hand watch belt or with one side of adhesive. Rings, mounted on a finger, also may be of use. The said device can be embodied as solid ring, inside a watch or as a wrap around the arm and secured in place by an n elastic band, by Velcro or with a belt and buckle. The said device can be embodied as a patch with one adhesive side to secure it in place on the back of the palm and on the arm or in the form of a ring that is worn on the fingers. Also, the device adjusted to be integrated with any kind of utensils, spoon, fork and the like, may be used as an add on, or fully incorporated into utensils.

The external device may include weight system, as a non limiting example a force transducer, or a strain gauge, hence weighing, each bite size. Another sensing capability is an oscillating member as published by T Gast 1985 J. Phys. E: Sci. Instrum which changes its frequency with added mass of food, or with taking food out of the utensil. The device may further include thermometer available from Sensorsoft Corporation, Ontario Canada on any available utensil, or drinking container, in a form of thermal sensor, capable of detecting a change of temperature, either of food, (hot cold), the delivery of food from a utensil, into the mouth, and the like. The main event generation is ΔT. This ΔT event sets a flag that there is a change from room temperature, either low (cold food) or high (hot food). From this e can deduce that food is present on said utensil. When delivered, there is also a change as ΔT. From this change we can deduce that food been delivered into the mouth. This change sets another flag, updating microcontroller 320 or microprocessor 420, via corresponding communication means, that a bolus of food has been delivered.

The said external device may be personalized with a setup function that will enable the user to set up the hand angle and position at the first meal used thus creating a personalized baseline angles of range of motion. Another embodiment may include a calibrating function, allowing gathering sequential volume or weight of food consumed by the user, and inserted to calculation via communication port, or local button. The operation may be a key in of data or scroll between pre set volume or weight values. The said device may have a start button the user starts the device at the beginning of a meal, and for stopping meal period. Moreover, the end of the monitoring of the meal may be automatic and the time from end of meal signal to shut down will be long enough with a random timing each meal. And is used as an actuator of the measured change in the pressure monitored signal. The combination of the hand motion and position device and the measured pressure pattern enables us to differentiate various measured signals such as eating from vomiting or saliva swallowing and to distinct between drinking by glass or by straw and liquid food eating with spoon. The addition of this device provides further important medical and behavioral information that can help surgeon distinct liquid food eaters more precise and advise them on behavioral modification.

The proposed device collects the motion data and time of event and transmits it to the pressure data logger in real time, if the motion detected correlates with a eating or drinking motion then the pressure monitoring device records the events as a validated meal or a drinking event if the motion detection is absent then the data collected should be regarded as non validated stored in a separate log and analyzed by a different algorithm assuming mal function of the hand held device, non compliance behavior by not wearing or not operating it or using the other hand without the motion detection device for these eating or drinking events. The proposed device can assist as well to estimate the duration of time between food bolus reaching the mouth time of chewing the food or holding it in the mouth as the difference between the time of food getting to mouth less the time of pressure onset in the band minus 7 seconds (the time food passes through the esophagus) (Tm−Tp−7 sec=Tc) this information is important for the training and education of the patient with this important component of the eating behavior, and it improves the accuracy of the system in differentiating not enough chewed food bolus from other events such as accidental ingestion of less chewable bite of food.

Figure 4B:
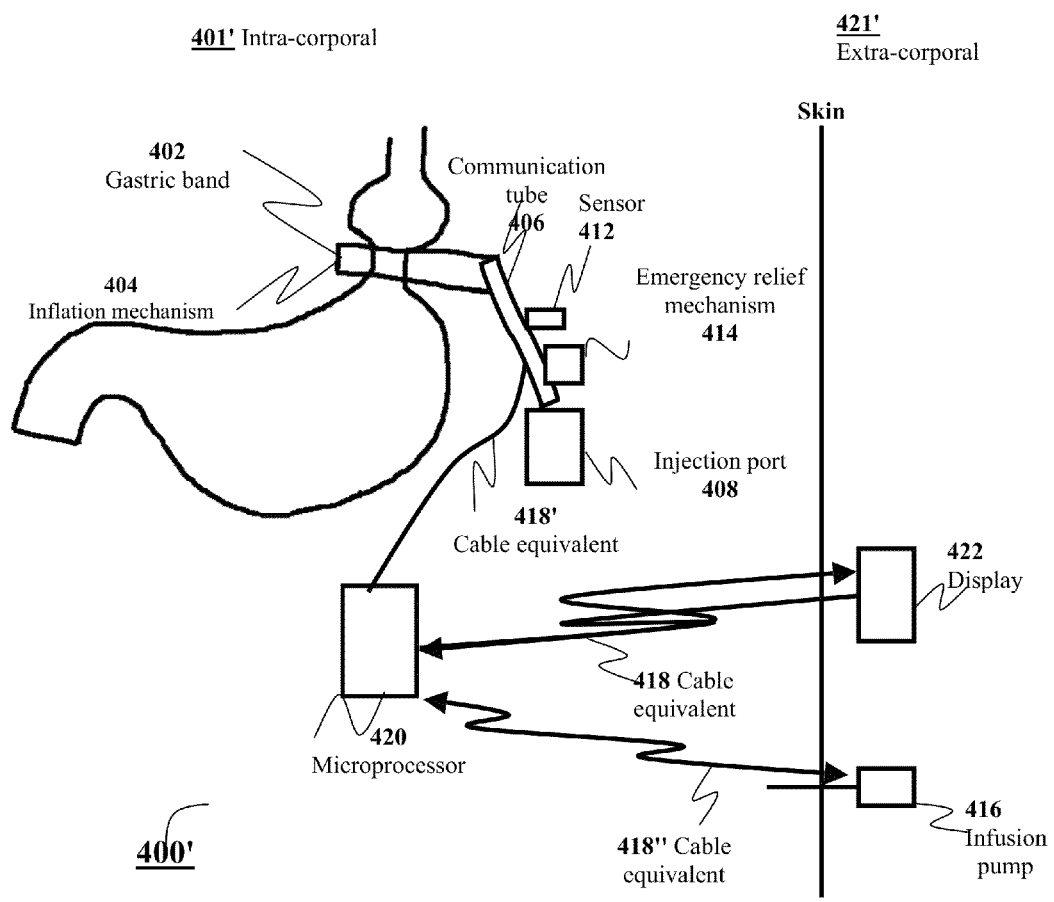
FIG. 4B shows yet another embodiment of an apparatus of the invention including infusion pump.

FIG. 4B shows another embodiment of an apparatus of the invention in the form of an apparatus 400'. As in apparatus 400, apparatus 400' includes an intra-corporal section 401' and an extra-corporal section 421'. Section 401' includes a gastric band 402 with an inflation mechanism 404, a communication tube (hydraulic line) 406 and a common injection port 408. In some embodiments of apparatus 400, a sensor 412 and an emergency relief mechanism 414 may be connected via communication tube 406 in any position along communication tube 406. In some embodiments, sensor 412 and emergency relief mechanism 414 may be connected by a cable equivalent 418'. In some embodiments, sensor 412 and emergency relief mechanism 414 may be directly combined with gastric band 402 in a single unit. In some embodiments, sensor 412 and emergency relief mechanism 414 may be combined with a microcontroller 420 in a single unit and be in communication with gastric band 402 via a cable equivalent 418' and communication tube 406. An infusion pump 416 is coupled to microprocessor 420 via a cable equivalent 418". Apparatus 400' may further include a display 422 for displaying to the patient indications related to eating behavior, eating behavior modifications and administration of substances. Display 422 and microprocessor 420 communicate via cable equivalent 418.

Figure 5A:
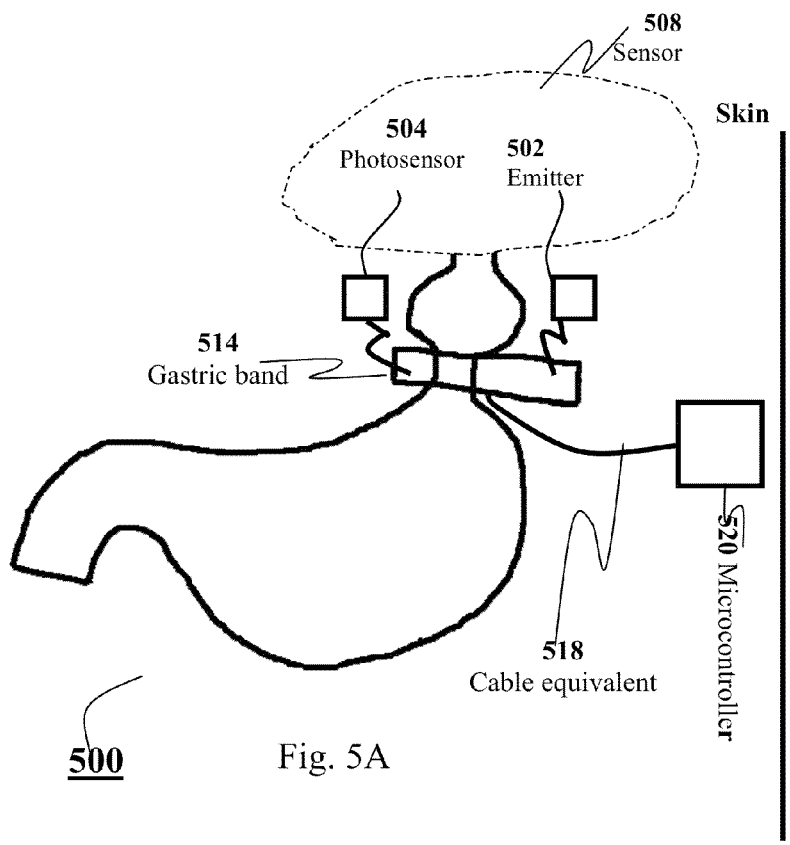
FIG. 5A describes an implanted optical sensor arrangement in an apparatus of the invention.

In some embodiments, sensors 108, 312 or 412 may be optical sensors and in particular infrared (IR) sensors. FIG. 5A describes an implanted optical sensor arrangement in an apparatus of the invention. An optical sensor system 508 includes an optical emitter 502 optically coupled to a photo-sensor 504. Emitter 502 and photo-sensor 504 may be positioned on opposite sides of a gastric band 514 or, optionally, may be positioned on the same side of gastric band 514. System 508 communicates with microcontroller 520 via a cable equivalent 518. In some embodiments, system 508 operates in the near infrared (NIR) spectrum range. In use, a reflective test fluid, for example a fluid that reflects infrared light, is ingested by the patient. The flow of the reflective test substance will result in IR light reflected onto photo-sensor 504, while the absence of the reflective test substance will result in little or no IR light reflected onto photo-sensor 504. Similar effects may be achieved using transmission instead of reflection. It is known that specific wavelengths and harmonies in the IR spectrum of food are directly connected to food fat, carbohydrates and protein content. In other words, an IR signal detected by the sensor can be translated by well known ways into macronutrient contents. In the embodiment above, a positive IR signal will be indicative of a flow condition, while the absence of a signal will be indicative of a no-flow condition. Sensor system 508 may be coupled to an implanted microcontroller 520, which can communicate with extra-corporal components.

Figure 5B:
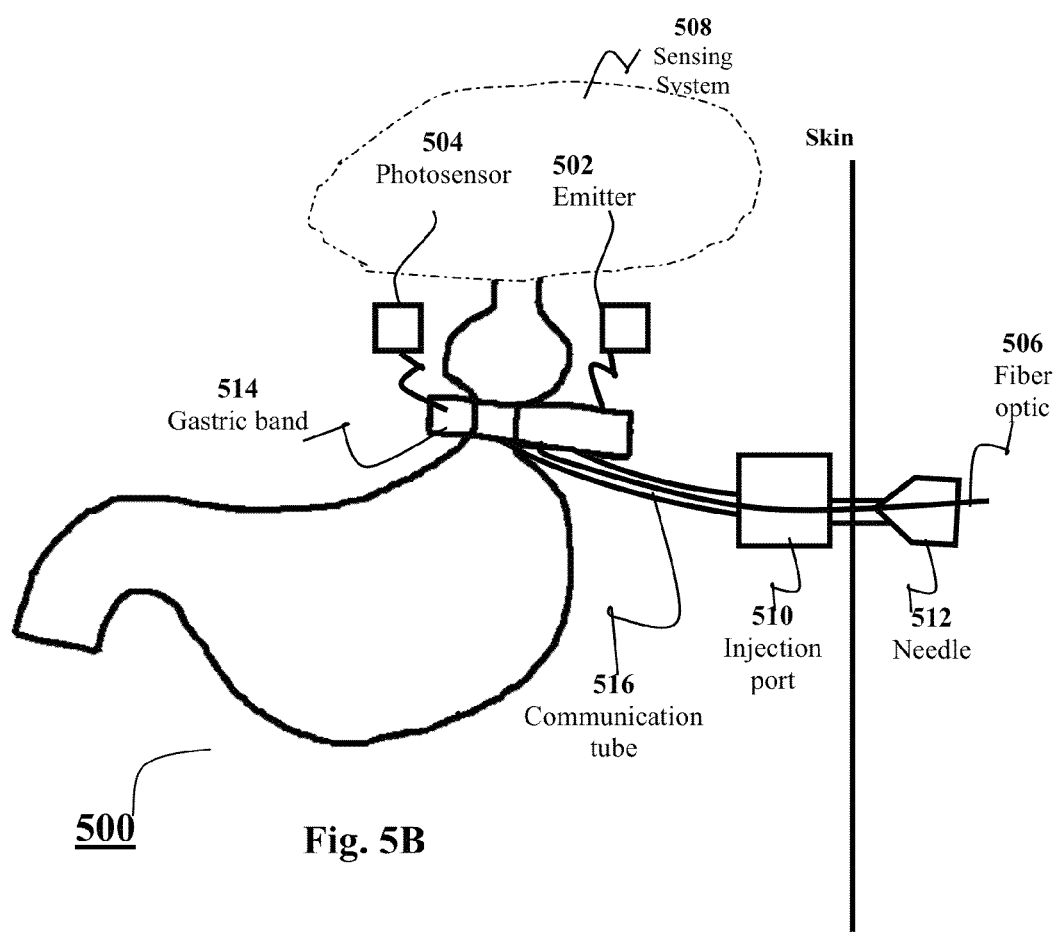
FIG. 5B shows an extra-corporeal optical sensing arrangement for an implanted apparatus of the invention.

FIG. 5B shows an extra-corporeal optical sensing arrangement for an implanted apparatus of the invention. The optical sensor system is the same as in FIG. 5A, but access to it is from external sources such as fiber optic 506, through an injection port 510, a needle 512 and a communication tube 516. The IR source and the IR sensor may be extra-corporal, with the IR light provided to gastric band 514 through suitable fiber optic means and the reflected IR light collected to the extra-corporal sensor through similarly suitable fiber optic means, as well known in the art. It is also possible to use such arrangements with common adjustable gastric bands (AGB) known in the art.

Figure 6:
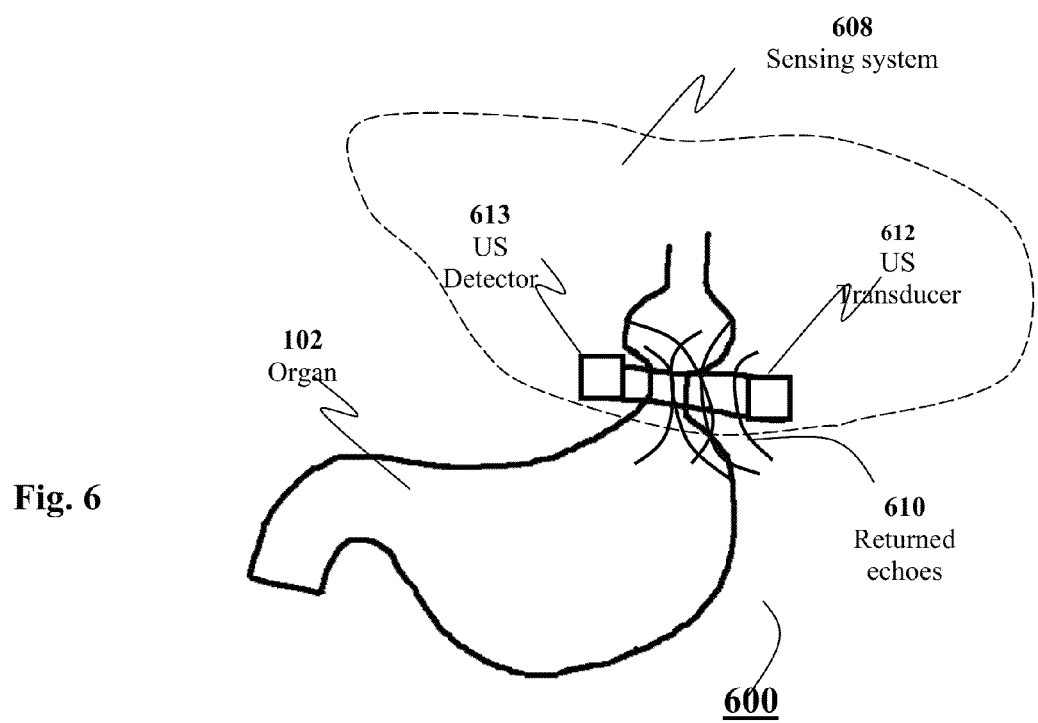
FIG. 6 shows a gastric restriction apparatus that includes an ultrasonic sensing element with an active transducer and a detector.

In some embodiments, sensors 108, 312 or 412 may be ultrasonic (US) sensors. FIG. 6 shows an apparatus 600 that includes an ultrasonic sensing element 608 with an active (electrically vibrating) US transducer 612 and a US detector 613, which are well-known in the art. Element 608 may be implanted within the inner surface of device 600 or placed immediately next to the device. The precise location of the transducer is not critical to operation, as long as the location is such that transducer 612 can effectively permit the detection of the test substance as it moves from the upper stomach pouch to the lower stomach pouch through the stoma orifice of organ 102.

Sensing element 608 may be configured to vibrate at a frequency in a range of from about 1 MHz to about 30 MHz. In some embodiments, the transducer is configured to vibrate in a range from about 5 MHz to about 15 MHz. An angle θ is defined as the angle of incidence between the pulses and the direction of fluid flow:

$$f_D = 2 f_t V \cos \theta$$

where $f_D$ is the Doppler frequency, $f_t$ is the vibration frequency, c is the speed of sound in tissue and V is the measured velocity of the fluid or object in motion. Solving for velocity:

$$V = f_D/(2 f_t \cos \theta)$$

Depending on the acoustic impedance of the material into which the output pulses are directed, the ultrasound output may generate return echoes 610. Return echoes are most efficiently created when there is a difference in the acoustic impedance between two regions or materials. For example, a stoma orifice without any substance will return an echo different from a stoma orifice filled with a substance. When a food substance passes through device 600, the added pressure and peristaltic motion may be measured by device 600 as a change from the stoma orifice without any substance. This change may be detected by acoustic impedance mismatch.

Figure 7:
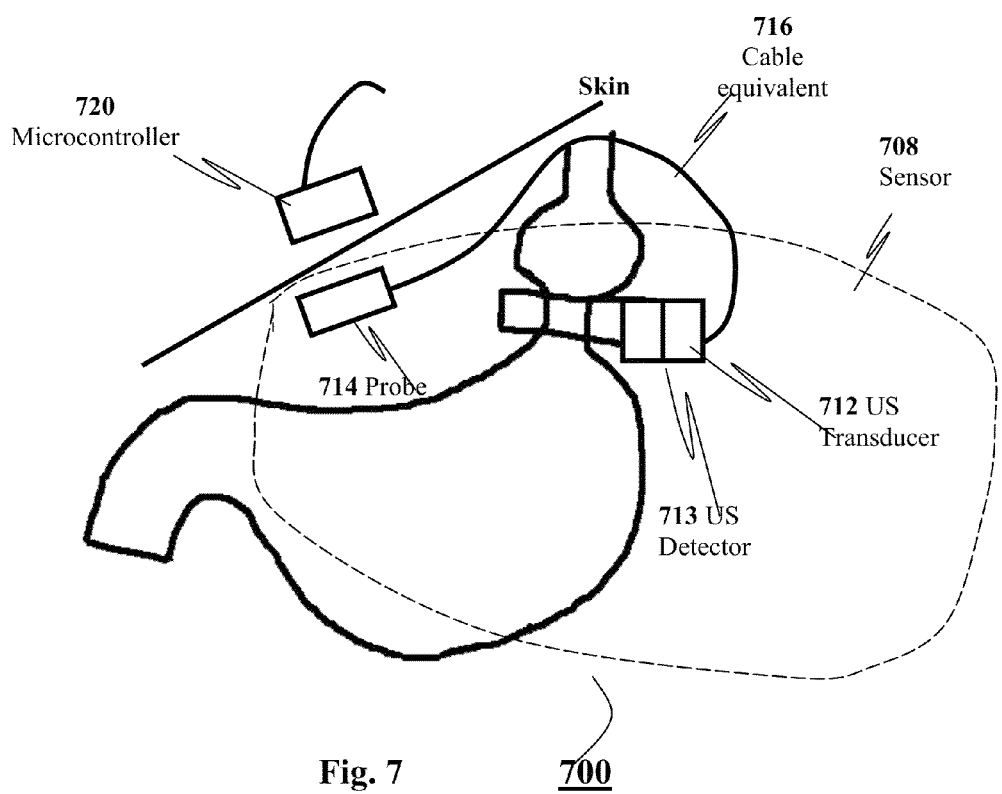
FIG. 7 shows a gastric restriction apparatus that includes a passive ultrasonic sensing element.

FIG. 7 shows an embodiment of an apparatus of the invention in the form of an apparatus 700 that includes a passive ultrasonic sensing element 708. Element 708 includes a US hydraulically vibrating transducer 712 and a US reflector 713, coupled via a cable equivalent 716 to a probe 714. Element 708 is configured to be implanted in the patient, for example subcutaneously or intra-abdominally. In this configuration, the implanted device requires no active electronics to power it. Power is applied from the outside, controllable via an external microcontroller processor 720 placed on the patient's skin. A signal is generated by microcontroller processor 720. The ultrasound pulses which are created are propagated through the skin and fat to probe 714. Return echoes are transferred through cable equivalent 716 to US transducer 712 resulting in oscillations. These oscillations produce a signal which is then transferred via device 700 to US reflector 713. The reflected signal mismatch between the anticipated reflection and an actual reflection is transferred to a microcontroller 720 for further analysis and display. This results in US detection of a bolus passage through the stoma.

The flow of a substance (solid or liquid food) sensed by the sensor may be described as similar to flow through a "modified" orifice plate flow meter. The present inventors have determined that in the case of a gastric band, "modified" Navier-Stokes equations may be used to describe the substance flow rate, Reynolds number, mass flow, velocity, and volumetric flow. The "modified" terminology relates to the external force component of the peristaltic motion and to the influence of stoma diameter change during food passage (flexible tube vs. rigid tube). The derivation of these equations is given next.

Derivation of Modified Navier-Stokes/Bernoulli Equations

The derivation begins with the conservation of mass, momentum, and energy being written for an arbitrary control volume. In an inertial frame of reference, the most general form of the Navier-Stokes equations can be written as:

$$\rho \left( \frac{\partial v}{\partial t} + v \cdot \nabla v \right) = -\nabla p + \nabla \cdot \mathbb{T} + f, \tag{1}$$

where v is the flow velocity, $\rho$ is the fluid density, p is the pressure. $\mathbb{T}$ is the (deviatoric) stress tensor, f represents body forces (per unit volume) acting on the fluid and $\nabla$ is the del operator. This equation is often written using the substantive derivative, making it more apparent that this is a statement of Newton's law:

$$\rho \frac{Dv}{Dt} = -\nabla p + \nabla \cdot \mathbb{T} + f. \tag{2}$$

The terms on the right side of the equation represent the body acting forces, the pressure gradient, and the forces due to the viscosity of the fluid. The body acting forces are proportional to the wetting behavior between the particles, surface and shape and the liquid part of the body of fluid. The velocity field is proportional to the pressure drop field. This field may oscillate, and create average downstream flow, intermittent flow or upstream flow. When the substance is composed of a liquid solution, flakes, flow in long constrictions with a small lumen diameter, flow separation regions, or turbulent energy losses in cases of severe stenosis, reduce the energy content of the fluid, and may also plug the flow.

In peristaltic motion, we can observe periodical pressure changes. However, opening pressure of the lower esophageal sphincter is proportional to pressure drop due to the stoma which may be created by gastric restriction device. The sum of peristaltic and other forces, generate another pressure which further facilitate movement of a substance within the lumen. Fluid or food does not typically pass through the stoma at a steady rate. Peristaltic contractions typically cause an intermittent or periodic flow rate reading in real time. The peak flow rate during this period can be an indicator of the effect of a tight restriction, predicting for example the likelihood of esophageal dilatation. In addition to the peak flow rate, the frequency or consistency of the peristaltic contractions (i.e., the number of contractions per time) can also be determined. By identifying typical patterns of test flow traces, patients can be grouped by severity of esophageal condition or by peristaltic pattern, to help determine not only how tightly their restriction should be adjusted, but also, for example, whether a more conservative diet should be selected.

The peristaltic phenomenon can be used in conjunction with the real time flow measurement. For example, the restriction device may be tightened completely, causing complete occlusion at the stoma. The restriction device may then be slowly loosened until the desired stoma size is reached. By assessing a group of several peristaltic pulses, different degrees of stoma tightness can be more easily compared, without the need to ingest a large amount of a calibration food standard.

In order to more accurately describe flow through a gastric band, the basic Navier-Stokes equation is modified as follows $$\rho \frac{D \vec{V}}{Dt} = \rho \vec{B} - \nabla p + \mu \nabla^2 \vec{V} + \vec{F} \delta(x, y, z, \varphi, \theta, t, S) \tag{3}$$

where B represents a body force acting on a particle inside the fluid, and where the added component $\vec{F} \delta(x,y,z,\varphi,\theta,t,S)$ of force per unit of shape depends on position (x,y,z), direction ($\theta, \varphi$), time (t), and on a value S that represents shape. S relates to volume, surface area of the body of fluid, moment of inertia, gyration radii and other dynamic functions, generated by the travel of a fluid particle in the medium. The time (t) may be substituted with frequency (1/t). Of course, $\delta(x,y,z,\varphi,\theta,t,S)$ may be a function, independent or dependent of any of its components Expanding formula (3) gives $$\rho \frac{\partial \vec{V}}{\partial t} + \rho \vec{V} \cdot \nabla \vec{V} = -\nabla p + \rho \vec{g} + \mu \nabla^2 \vec{V} + \vec{F} \delta(x, y, z, \varphi, \theta, t, S) \quad (4)$$

where $$\rho \frac{\partial \vec{V}}{\partial t}$$

is the local acceleration, $\rho \vec{V} \cdot \nabla \vec{V}$ is the convective acceleration, $-\nabla p$ is the pressure force per unit volume, $\rho \vec{g}$ is the body force per unit volume and $\mu \nabla^2 \vec{V}$ is the viscous forces per unit volume. and $\vec{F} \delta(x,y,z,\varphi,\theta,t,S)$ is an externally added component of force per unit of shape. $\vec{F} \delta(x,y,z,\varphi,\theta,t,S)$ may also represent the ability of the tissue in described tract to accommodate pressure, i.e. pouch enlargement and pouch slippage.

Looking into said externally added component of force, we can also integrate the peristaltic component of the esophagus & Lower esophagus sphincter (LES) into the measurements.

The esophagus & LES behavior was described for example by Ghosh at all, Am j physiol gasrointest liver physiol 2007: 293:g1023-8, hence taking into account the peristaltic motion of the esophagus & LES as a peak Of 20 to 150 mm Hg, with contraction length between 10 to 30 seconds, we can filter the influence of the esophagus & LES, using standard mathematical approximations, out of additional bolus of food taken, shorter timeframe on low pressure may indicate an easy passage of bolus (liquid for an example,) and pressure peaks, i.e., contractions of the esophagus & LES, over pressure recorded above calibrated baseline (basic stoma adjustment without any bolus at all), may indicate the way in which the esophagus & LES forces the bolus to pass through the stoma. Changing of sitting or body position, may also influence the pressure of food passage the AGB. Such an influence may be integrated into the force equation by using an external position device, for example a vertical position indicator, a MEMS gyro and the like, and also may be filtered out by the same manner as the influence of the esophagus & LES, without the added flag of vertical position indicator. Intra band measurements indicating no esophagus & LES peristaltic motion, may indicate also complications such as band slippage band erosion etc. As a non limiting example, an In vitro apparatus was built, using heart pump, Homodynamics Israel, capable of adjustable stroke and frequency, an AGB over latex tubing, adjusted as 20 mm Hg basic pressure line. A bolus imitator made out of a piston divided into two compartments, one filled with physiological solution and the other with three types of food. One can be considered as liquid food, the other as semi liquid, made out of one part rice, boiled for 30 min in 3 parts water, a solid made out of one part rice boiled 20 min in 1.5 parts water. Each stroke was calibrated to 10 cc as to bolus administration. Ones the bolus was administered into the latex tubing, stroke was changed to reciprocating motion of 1 cc at 100 mmHg every 20 seconds. Data from the AGB port was retrieved using an 23 G Houber needle, connected to AGB port on one side and Pressure transducer available from Elcam israel on the other side. Data was collected using National instruments A/D USB 6009 data logger. Data was filtered and presented using Labview software available also from national Instruments.

Examination of the above equation shows that each term has units of force per unit volume, or $F/L^3$. Therefore, $\vec{F} \delta(x,y,z,\varphi,\theta,t,S)$ satisfies the basic equation, since if we divide each term by a constant having those same units ($F/L^3$) we obtain a dimensionless equation. Furthermore, the viscosity and specific gravity values also change.

Common Orifice Plate Flow Meter

In the following equations, the symbols used are as follows: $D_1$ is pouch diameter, $D_2$ is stoma diameter, $P_1$ is upstream pressure, $P_2$ is downstream pressure, v is kinematic viscosity, $\mu$ is dynamic viscosity and $\rho$ is upstream density. The calculation of flow rate using an orifice plate is for incompressible flow, based on the Bernoulli principle $$\frac{p_1}{\rho} + \frac{v_1^2}{2} + gz_1 = \frac{p_2}{\rho} + \frac{v_2^2}{2} + gz_2 + \frac{\Delta p_{1-2}}{\rho} \quad (5)$$

where V is the velocity of the food through the stoma, g is the gravitational constant (9.81 m/s$^2$) and z is the geodetic height. Assuming that the pressure lost is negligible (the pressure drop is obvious and included with the coefficient of discharge which is introduced below):

$$\Delta p_{1-2} = 0$$

and $$gz_1 = gz_2$$

and if velocities are substituted with flow rate $$V_1 = \frac{4Q}{\pi D_1^2} \quad V_2 = \frac{4Q}{\pi D_2^2} \quad (6)$$

where $V_1$ and $V_2$ are respectively the upstream and downstream velocities before and after the stoma orifice, Q is the volumetric flow rate and D is diameter. The pressure drop through the orifice because of velocity increase can be calculated as follows:

$$\frac{p_1 - p_2}{\rho} = \frac{1}{2}\left(\frac{16Q^2}{\pi^2 D_2^4} - \frac{16Q^2}{\pi^2 D_1^4}\right) \quad (7)$$

Expressing the flow rate from the previous equation leads to:

$$Q = \sqrt{\frac{1}{1-\left(\frac{D_2}{D_1}\right)^4}} \frac{\pi D_2^2}{4} \sqrt{\frac{2(p_1 - p_2)}{\rho}} \quad (8)$$

Substituting:

$$E = \sqrt{\frac{1}{1-\left(\frac{D_2}{D_1}\right)^4}}$$

the flow rate can be determined as:

$$Q = CeE\frac{\pi D_2^2}{4}\sqrt{\frac{2(p_1 - p_2)}{\rho}} \qquad (9)$$

where C is the coefficient of discharge and e is an expansion coefficient. C can be calculated using following equation (ISO):

$$C = 0.5961 + 0.0261\beta^2 - 0.216\beta^8 + \qquad (10)$$
$$0.000521\left(\frac{10^6\beta}{Re_D}\right)^{0.7} + \left(0.0188 + 0.0063\left(\frac{19000\beta}{Re_D}\right)^{0.8}\right)\left(\frac{10^6}{Re_D}\right)^{0.3}$$
$$\beta^{3.5} + (0.043 + 0.08e^{-10L_1} - 0.123e^{-7L_2})\left(1 - 0.11\left(\frac{19000\beta}{Re_D}\right)^{0.8}\right)$$
$$\frac{\beta^4}{1-\beta^4} - 0.031\left(\frac{2L_2}{1-\beta} - 0.8\left(\frac{2L_2}{1-\beta}\right)^{1.1}\right)\beta^{1.3}$$

where $\beta$ is the diameter ratio $D_2/D_1$. $Re_D$ is the Reynolds number which can be calculated as follows:

$$Re_\rho = \frac{VD}{\upsilon} = \frac{\rho VD}{\mu} \qquad (11)$$

where $\upsilon$ is kinematic viscosity, $\mu$ is the dynamic viscosity and $L_1$ and $L_2$ are empirical functions that relate to the particular organ through which the flow is measured. The mass flow is now given by $$G = \rho Q \qquad (12)$$

and the velocities $$V_1 = \frac{4Q}{\pi D_1^2} \quad V_2 = \frac{4Q}{\pi D_2^2} \qquad (13)$$

The abovementioned mathematical development enables obtaining measurable parameters of an instantaneous event and converting them into a "description" of food flow through the tract. This description creates meaning to volume, flow and time, which can be processed into eating behavior variables.

Figure 8:
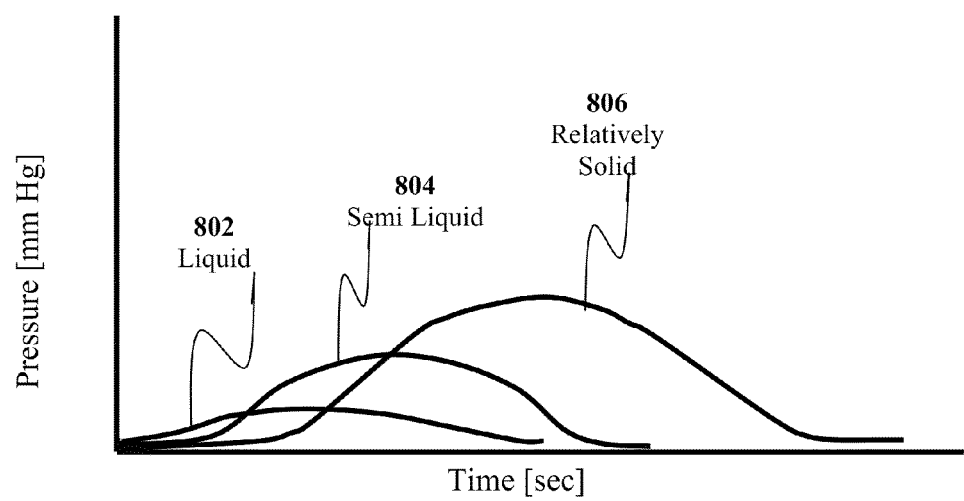
FIG. 8 shows different pressure-time curves for standard foods having different viscosities passing via the stoma orifice.

FIG. 8 shows different pressure-time curves for standard foods having different viscosities passing via the stoma orifice. The same standard foods may be ingested differently by different patients. In some cases, standard foods may be produced from regular foods and tested for viscosity using techniques such as Ford Cup. The graphs, obtained using an apparatus of the invention such as apparatus 100, show the behavior of liquids 802, semi-liquids 804 and relatively solid foods 806. The pressure-time curves show different patterns for different food viscosities. This information may be gathered into a database and displayed to the patient, among others to motivate the patient to change his/her eating behavior. Each and every graph is characterized by positive or negative sign slope with $\Delta P/\Delta t$ and a portion of relatively flat zone. The positive $\Delta P/\Delta t$, is considered as pressure rise, and the negative component as pressure drop. The relatively flat zone is considered as negative or positive slope with $\Delta P\Delta t<\frac{1}{6}$ (One sixth) of common slope rise or drop. Hence, operating $\Delta P/\Delta t$ we can get the change in the graph. Out of this change we can calculate the filtered graph without the esophagus & LES pressure influence and also an event graph.

The results demonstrate the following waveform behavior after filtering out the influence of the esophagus & LES. vertical axis represents synthetic values of pressure, after being filtered and normalized mathematically, and horizontal axis represents units of time in seconds Reference is now made to FIGS. 15A-G which illustrate a non limiting example of some working descriptive examples deduced from the measured data that are related to eating behavior patterns.

Figure 15A:
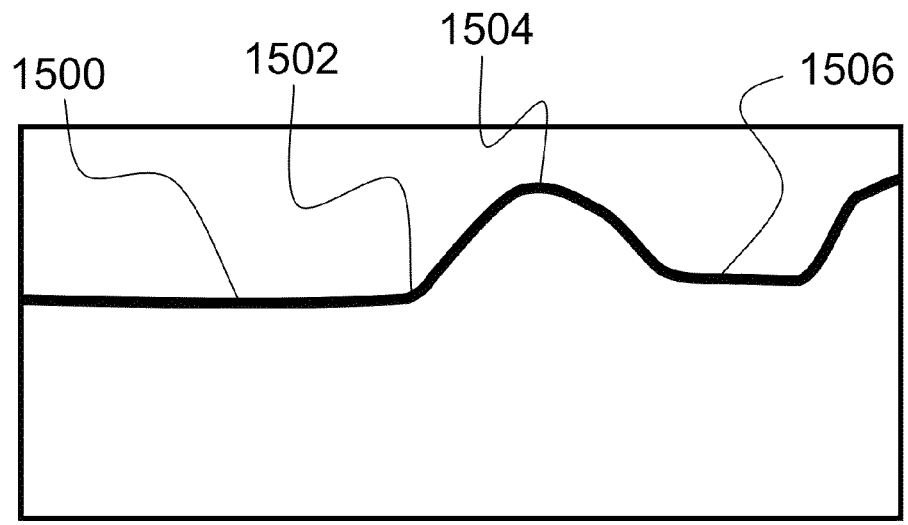
FIG. 15A-G provides a non limiting example of some working descriptive examples deduced from the measured data that are related to eating behavior patterns.

FIG. 15A illustrates Liquid bolus passage through the band.

It is seen that there is a baseline 1500 of known pressure, however $\Delta P/\Delta t$ is almost zero. Then a positive slope begin from 1502 to a peak 1504, and than a negative slop from 1504, to known level beginning 1506 which may be different from baseline 1500.

Figure 15B:
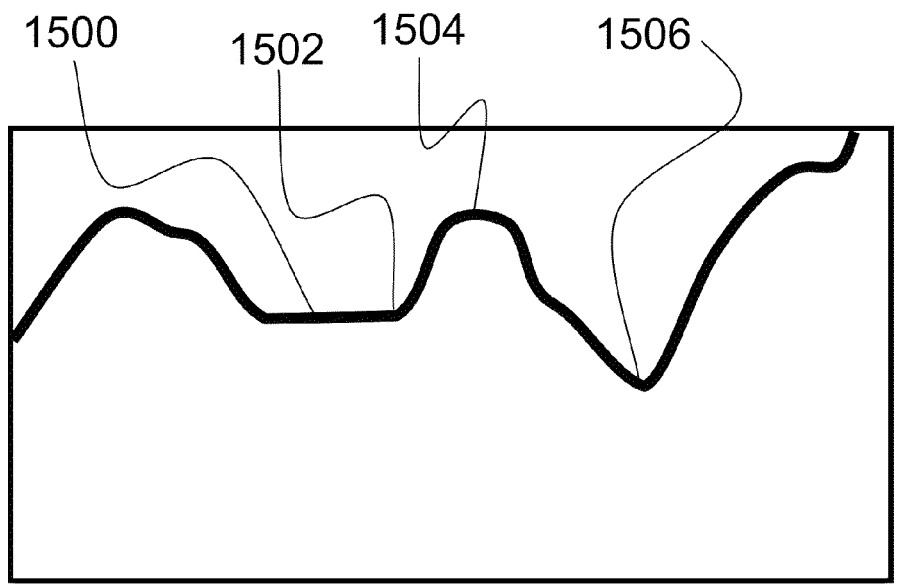

FIG. 15B illustrates Semi-Liquid bolus passage through the band This semi liquid graph is characterized by moderate positive slope from 1502 to 1504, and a steep drop from 1504 to 1506. 1500 represents baseline.

Figure 15C:
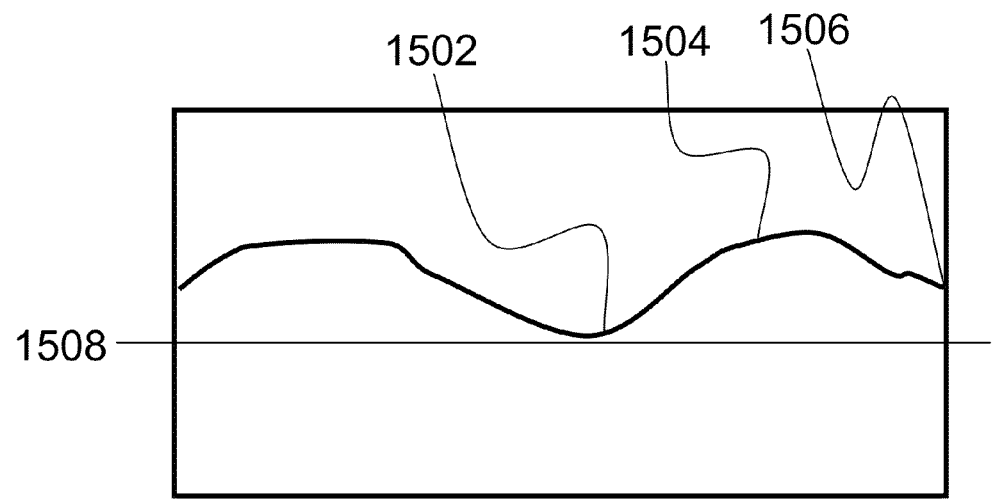

FIG. 15C illustrates Solid bolus passage through the band. This graph is characterized mainly by the product under the graph until 1508, with moderate or steep positive slope, from 1502 to 1504 or negative drop from 1504 to 1506.

Figure 15D:
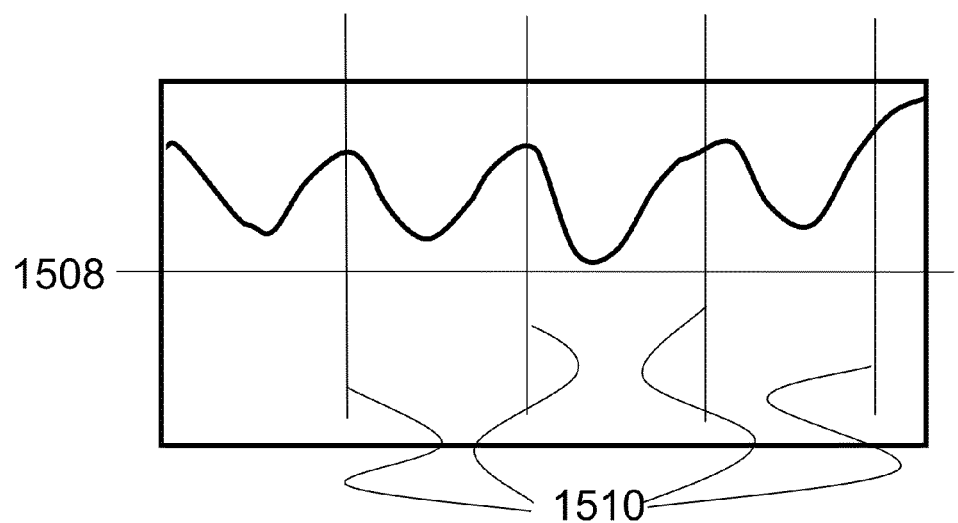

FIG. 15D illustrates Normal Eating rate of semi-liquid bolus it is seen that there is periodical 1510 correlation of speed of eating above baseline 1508.

Figure 15E:
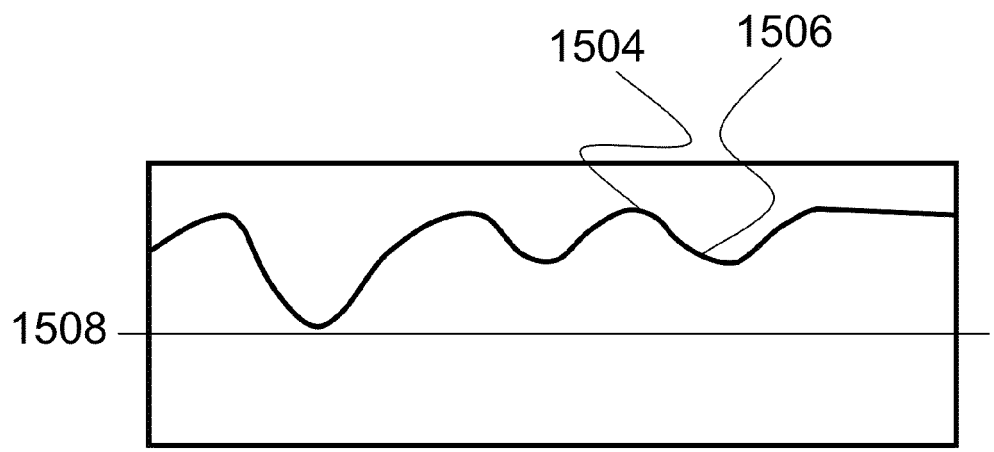

FIG. 15E illustrates Fast Eating rate of semi-liquid bolus. Fast eating is characterized by multiple peaks 1504 above baseline 1508, with high product under the graph and steep or moderate $\Delta P/\Delta t$.

Figure 15F:
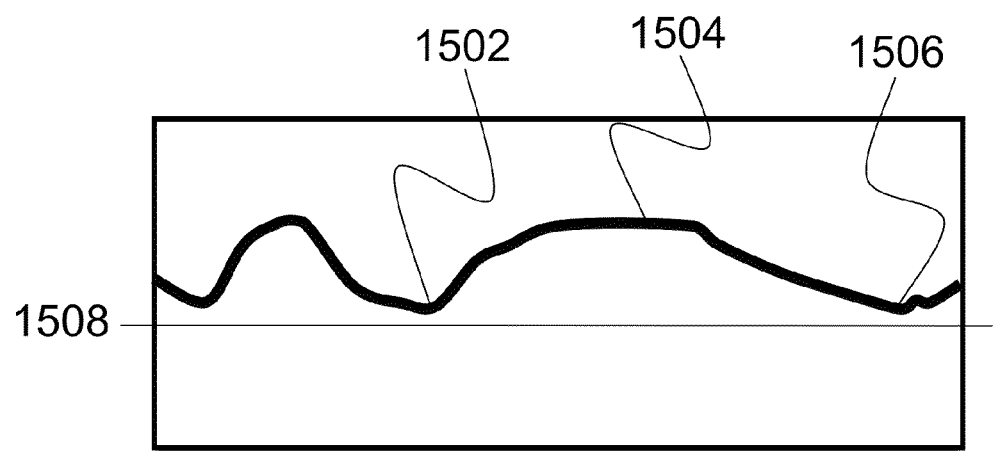
Figure 15G:
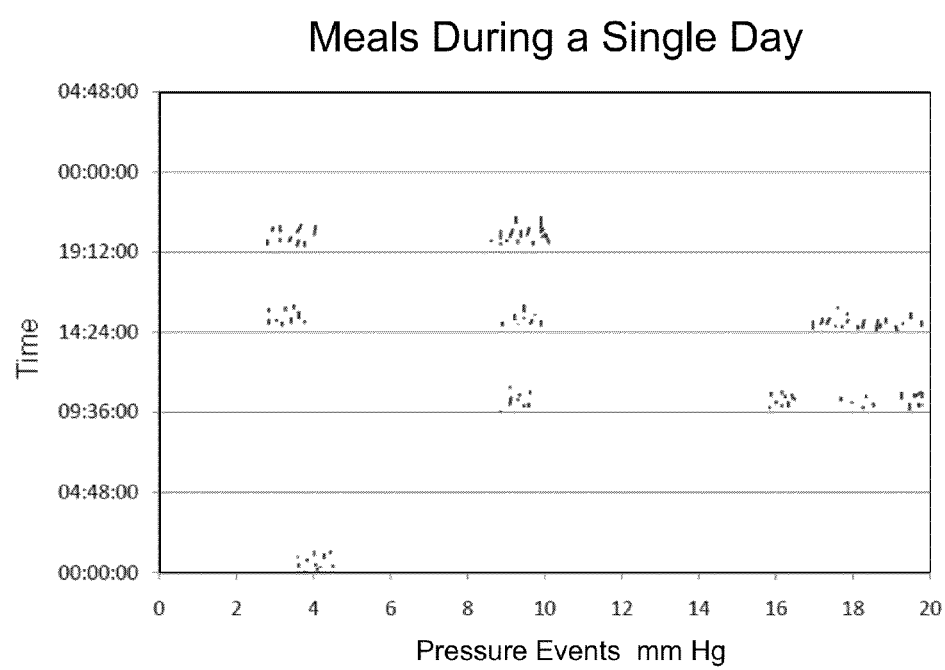

FIG. 15F illustrates passage of a bolus of food which was not chewed enough. This graph is characterized mainly by the product under the graph, between the baseline 1508 and the curve, with a steep positive slope from 1502 to 1504 and a moderate negative drop from 1504 to 1506.

From this working example we can build a daily event graph, capable of defining each product of eating behavior graphs as characterized by $\Delta P/\Delta t$, product under graph and number of peaks.

Such a graph is filtered of noise, without the esophagus & LES influence and $\Delta P/\Delta t<0.1$ of set pressure as described before, and represents a synthetic pressure points over a daily timeline. Integrating a clock, (available on any microcontroller or microprocessor operated system) into the sensed element of bolus passage, by any possible sensing element, one can determine the time of the day in which a bolus had passed the stoma.

In this way, it is possible to map every bolus, type of bolus (liquid, semi-liquid, solid) and daily occurrence. Such mapping allows a physician, a dietician or a patient to trace meals, snacks liquid consumption. In order to change mapping into consumed volume, a 10 cc volume may be considered as a baseline for volume. Although each patient physician or other person can modify the volume factor by dividing a known volume of food, by the number of bolus required to consume the food. Hence the volumetric correcting factor for a specific patient may be determined, for liquid, semi liquid and solid food.

Out of this map, we can determine eating behavior, if a person is a constant speed eater, night eater, total size of meal, average volume of meal, and average time of meal. Volumetric consumption by time, as required to pace the meal, a map with smaller then recommended solid food occurrences may indicate Shifting to liquid food, food tolerance may be indicated as a bolus which does not pass the stoma, or vomit as high peak pressure of 2-5 sec.

Since only points filtered under conditions described at FIGS. 8, 15, it is clearly seen that low pressure events from 0 to 1512, may represents liquid passage through the stoma, medium pressure events from 1512 to 1514, may represent well chewed food, or semi liquid food passage, and high pressure events from 1514 and up may represent not enough cowed or another indication of wrong passage of food through the stoma. By this approximation we can gather events of food passage.

Each of the points describes a pressure event that is a combination of time and pressure and is analyzed according to the algorithms described and mathematical model described in FIGS. 8, 9A, 9B, 10A, 10B. 11A, 11B, 11C. Out of this analysis we can generate the conclusions as described in FIG. 15A-G such as: FIG. 15A describes the pressure event of a liquid bolus passage through the band. It is seen that there is a baseline 1500 of known pressure, however ΔP/Δt is almost zero. Then a positive slope begin from 1502 to a peak 1504, and than a negative slop from 1504, to known level beginning 1506 which may be different from baseline 1500. FIG. 15B describes a Semi-Liquid bolus passage through the band This semi liquid graph is characterized by moderate positive slope from 1502 to 1504, and a steep drop from 1504 to 1506. 1500 represents baseline. FIG. 15C describes a solid bolus passage through the band this graph is characterized mainly by the product under the graph until 1508, with moderate or steep positive slope, from 1502 to 1504 or negative drop from 1504 to 1506. Out of the analysis of the various points on chart 15 as a sequence of pressure events during said meal we can obtain further information regarding certain eating behavior patterns such as described in the following charts but not limited to FIG. 15D-G. FIG. 15D describes as an example not limited to normal Eating rate of semi-liquid bolus it is seen that there is periodical 1510 correlation of speed of eating above baseline 1508. It can be seen that the pressure peak returns to the baseline 1508 periodically, this return to no pressure in the pouch above the band is a desired phenomena that the patient should be trained to perform through our device and method. FIG. 15E describes the reassure sequence of Fast Eating rate of semi-liquid bolus but not limited to. Fast eating is characterized as multiple peaks above baseline, 1508, with high product under the graph and steep or moderate ΔP/Δt 1506 that appears before the previous pressure peak 1504 returned to the base line 1508 and so on periodically with a higher pressure build up after a while. FIG. 15 F describes an event of passage of a bolus of not enough chewed bolus of food. This graph is characterized mainly by the product under the graph, to a baseline, with steep positive slope from 1502 to 1504 and moderate significantly longer negative drop from 1504 to 1506 then the standard for a solid standard during adjustment. Should this behavior proceed the sequence of pressures will build to a total higher pressure in the pouch and might continue after the meal. This kind of event is preventable by the use of our method and device by providing the patient the proper guidance.

Reference is now made to FIG. 9.

Figure 9A:
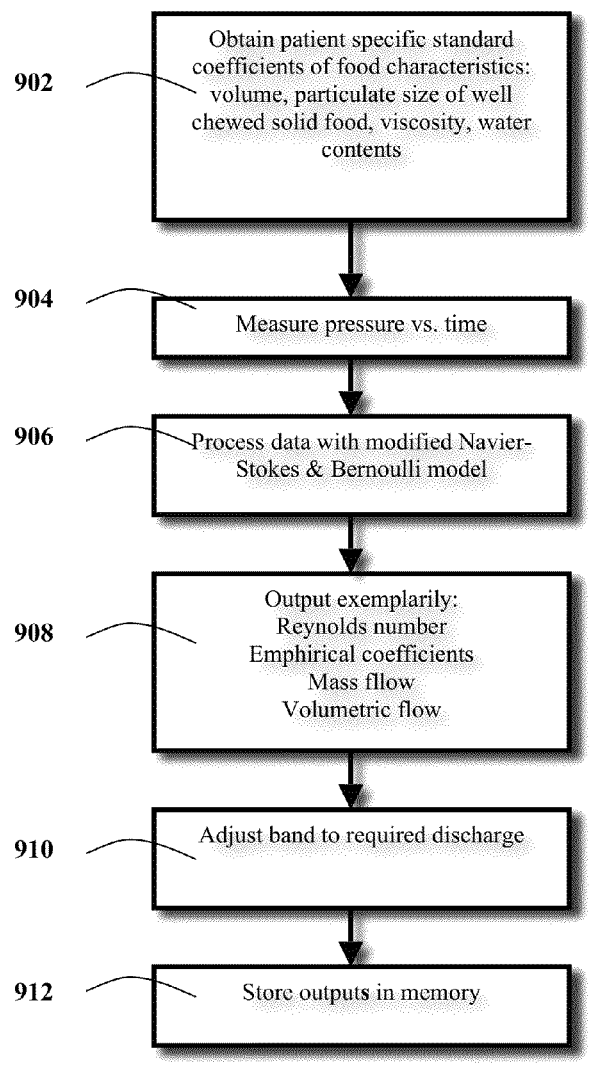
FIG. 9A describes a method for calibration of apparatus 100 based on the standard foods of FIG. 8.

FIG. 9A describes a method for calibration of apparatus 100 based on the standard foods of FIG. 8. In step 902, a patient is given a standard food with known properties. These may include viscosity, amount, division to standard bites (e.g. ranging from 2 cc to 50 cc), known particle size, water content and the like. The standard foods may be different for each patient based on individual weight loss program goals, produced from common foods and tested for viscosity. In step 904, pressure is sensed at various times and provides a pressure-time input to the system. In step 906, the pressure values are processed using the modified Navier Stokes/Bernoulli equations. The processing provides the following outputs in step 908: Reynolds number and patient specific emphirical coefficients. In step 910, the outputs are used by a physician to adjust the gastric band. In step 912, the outputs (including the coefficients) are stored in a memory.

Figure 9B:
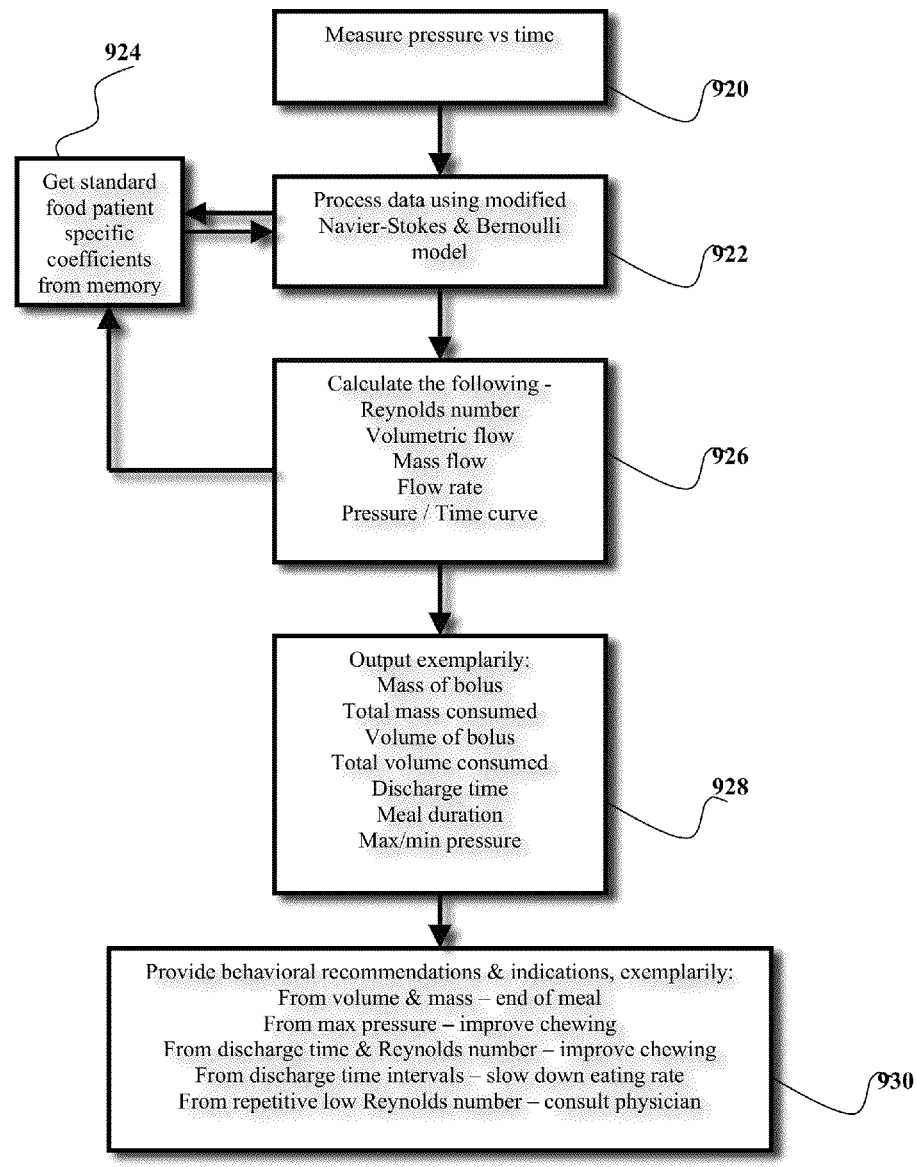
FIG. 9B describes the process of analyzing a bolus of food when the bolus passes the stoma orifice.

FIG. 9B describes the process of analyzing a bolus of food when the bolus passes the stoma orifice and relates also to the method described with reference to FIGS. 11A-11C. In step 920, pressure vs. time is measured as the food passes through the stoma orifice. In step 922, the pressure-time data is processed using the modified Navier-Stokes/Bernoulli equations. These equations are also fed standard empirical coefficients relevant to the type of food. In step 924, the data is compared to calibration values stored in memory. In step 926, processing of the data and the input of calibration values provides the following outputs: a Reynolds number, mass flow and volumetric flow, time of discharge, rate of flow and the like. Other outputs include the measured pressure vs. time. These outputs are used in step 928 to calculate "higher level data" such as bolus mass, total consumed mass, bolus volume, total consumed volume, discharge time, meal duration and maximum/minimum pressure. The higher level data is then used to provide recommendations to the patient and/or the physician or a caregiver in step 930. These recommendations may exemplarily include "next bite or wait—passage busy" (from sensed pressure) "end the meal" (from the volume and mass data), "improve chewing" (from the maximum pressure or from the discharge time and/or Reynolds number), "slow down your eating rate" (from discharge time intervals) or "consult physician" (recommendation to the patient from a repetitive low Reynolds number). When the patient follows these recommendations, eating behavior modification is provided per se.

Figure 10A:
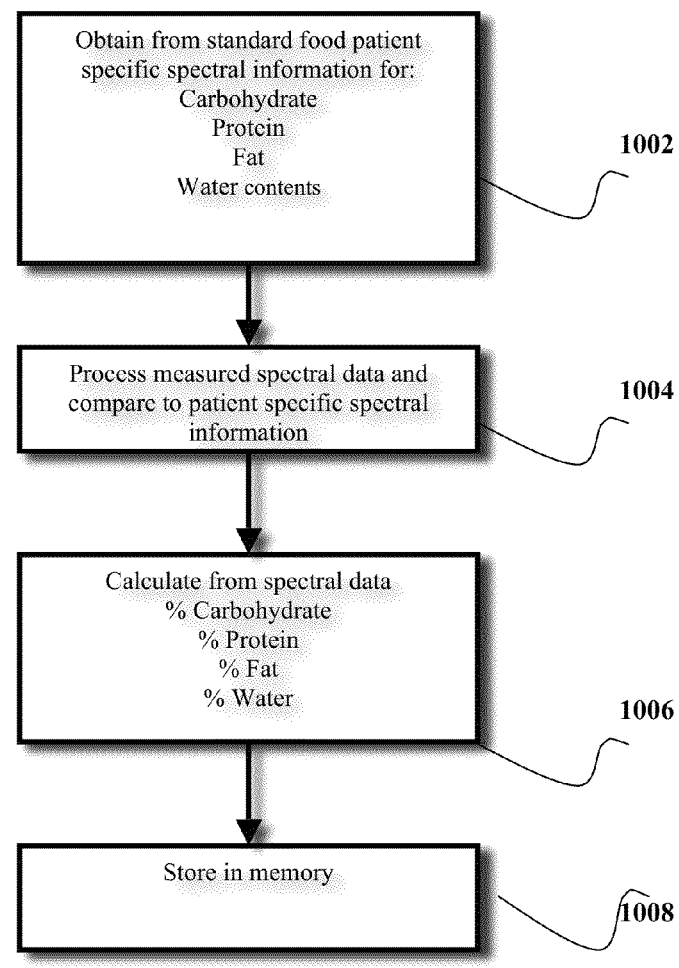
FIG. 10A describes a method for calibration of an apparatus of the invention based on standard foods caloric values using NIR technology.

FIG. 10A describes a method for calibration of an apparatus of the invention based on standard foods caloric values (known values of macronutrients) using NIR technology. As indicated in the description of FIGS. 5A and 5B, NIR provides the percentage of contents of macronutrients in a bolus. To calculate the caloric value, one needs the mass flow calculated from the modified Navier-Stokes/Bernoulli equations.

When a patient is given standard foods, different components such as fat, carbohydrates and protein absorb different wavelengths of the spectrum. In step 1002 NIR spectral data is acquired for these standard foods for each patient. In step 1004, the spectral data provides "standard" empirical coefficients related to percent of fat carbohydrates and protein for each patient. In step 1006, the percent of fat carbohydrates, protein and water is calculated from the empirical coefficients. In step 1008, the calculated percent of fat carbohydrates, protein and water for each type of standard food for each particular patient is stored in memory. Based on processed data, the physician may define a maximal caloric allowance of a meal, daily or for other periods, based on weight loss program goals for each patient.

Figure 10B:
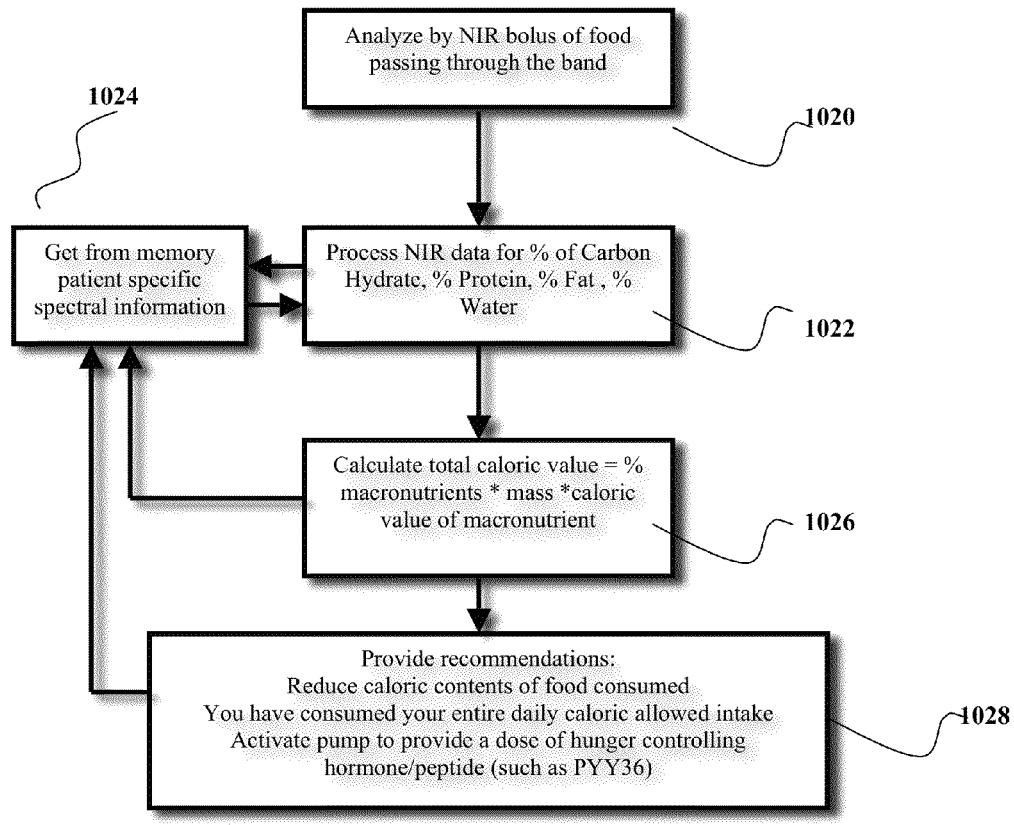
FIG. 10B describes an embodiment of a method for obtaining macronutrient contents using an apparatus of the invention with NIR technology.

FIG. 10B describes an embodiment of a method for obtaining macronutrient contents using an apparatus of the invention with NIR technology. Steps 1020 and 1022 parallel steps 1002 and 1004 in FIG. 10A. During the meal, the macronutrients contents of every bolus are calculated based on the NIR spectroscopy results, and the mass flow calculated from the modified Navier-Stokes/Bernouli equations above. The total caloric intake is calculated in step 1026. In step 1028, recommendations are provided to the patient, as described in more detail below with reference to FIGS. 11A-11C. As (or just before) the total caloric intake reaches a preset value, the system may generate an electronic signal sent by the cable equivalent to an internal or external pump that administers a preset volume of hormone or peptide such as PYY36 that controls hunger.

The following methods of use are described in detail with reference to apparatus 100, with the understanding that they may be performed with any other apparatus of the invention.

Eating Behavior Modification

In this method, apparatus 100 is used to provide inputs to a patient to change his/her eating behavior. This method takes advantage of the fact that the sensor data may be interpreted to illustrate "bad" and "good" eating patterns. The method is explained with reference to pressure as a particular sensed parameter, with the understanding that other sensed parameters obtained by NIR, ultrasound or other types of sensing may serve equally well for the stated purpose. FIGS. 11A-C show exemplary pressure-time data obtained with an apparatus of the invention.

Figure 11A:
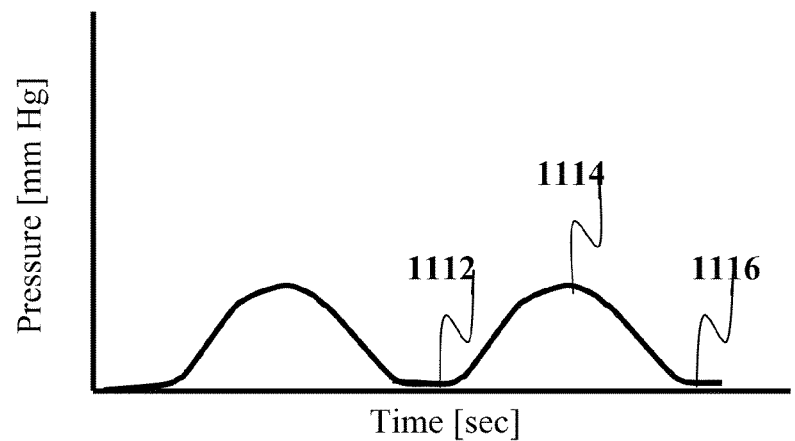
FIG. 11A describes a favorable eating behavior measured using an apparatus of the invention.

FIG. 11A describes a favorable eating behavior, exemplified by moderate pressure peaks 1114 and valleys 1112 and 1116 over time. Peak 1114 represents the presence of a bolus of food in the stoma, while valleys 1112 and 1116 represent an empty stoma orifice. This particular pressure vs. time behavior is observed when each bolus is taken only after clearing of the previous bolus from the stoma orifice. The pressure peaks are moderate, as no plug flow obstruction is present.

Figure 11B:
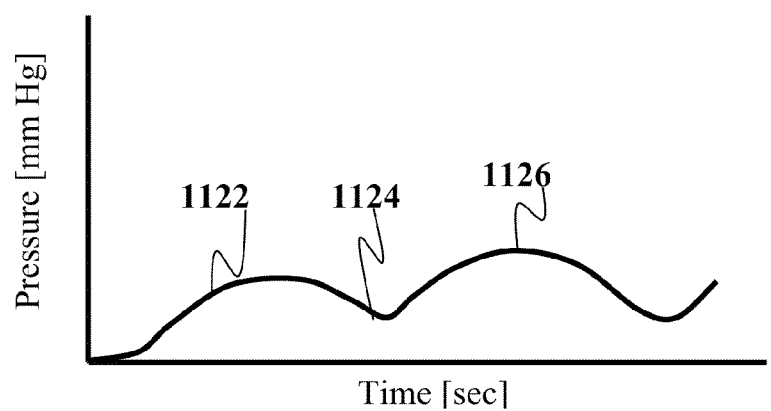
FIG. 11B describes a fast eating behavior measured using an apparatus of the invention.

FIG. 11B describes a fast eating behavior, exemplified by pressure-time pattern in which a next bolus, represented by a peak 1126, is taken before a previous bolus, represented by a peak 1122, was cleared from stoma orifice into the stomach, the clearance represented by a shallow valley 1124. As seen, valley 1124 is shallow, indicating non-complete clearing of the stoma orifice before the next bolus reaches it, i.e. representing a fast eating behavior.

Figure 11C:
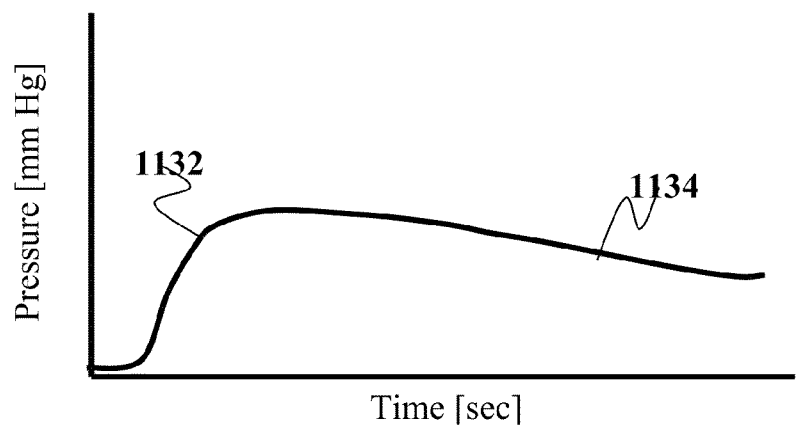
FIG. 11C describes a pattern behavior of un-chewed food measured using an apparatus of the invention.

FIG. 11C describes a pattern behavior of un-chewed food, exemplified by a pressure-time pattern that shows a larger integral under the curve. The food has high viscosity, can hardly pass the stoma orifice opening and exerts an elevated peak level of pressure 1132, creating plug flow and longer discharge time. 1134 represents the lack of a valley matching this behavior.

Assume it is desired for a patient equipped with an apparatus of the invention to change eating behavior from a "bad" one (exemplified by pressure-time curves similar to those in FIGS. 11B and 11C) to a "good" one (exemplified by the curve in FIG. 11A). The apparatus is used to acquire pressure-time curves in real time. The data in these curves is interpreted into commands to the inflation mechanism and emergency relief mechanism. The patient or the physician is presented with a graphic comparison between the pressure-time graph of the current bolus or meal and a graph of favorable behavior. The patient is then encouraged through recommendations as explained with regard to FIGS. 9B and 10B to change his/her eating behavior toward a favorable one.

After the band is properly calibrated and the basic values for the different monitored parameters are stored in the memory, it is possible to start monitoring the patient's eating behavior. For example, if the data is collected from the pressure sensor, as a pressure increase event is sensed, time recording, pressure recording, a bolus counter and the NIR sensor (when applicable) are set ON. The data collected is processed using the modified Navier-Stokes and Bernoulli equations to provide a volume description of the food flow through the gastric band. From the processed pressure-time curves, the apparatus can (by comparison of the data with stored standard constants and known values) deduce the different eating behavior conditions exemplified by FIGS. 11A-C ("good" or "bad"). As the pressure sensor senses food flowing through the band, the apparatus may provide a signal (for example a red light on the display turns ON) that the stoma orifice is "busy" and that he/she should stop eating. As the bite of food passes through the band and the pressure returns to baseline, the red light turns OFF and (for example) a second, green light turns ON, informing the patient that the food passage through the band is clear and that he/she can eat the next bite and so on. If the pattern of a bite following a bite in the manner that the passage emptying is respected as shown in FIG. 11A, the patient is provided (e.g. on the display) with a positive response regarding his speed of eating. If the pattern recorded resembles the pattern in FIG. 11B, then the patient is warned that he is eating too fast.

In terms of eating behavior interpretation, if the pressure-time curve shows that the food passing through the band had a maximal pressure equal or less than a "solid food standard" maximum pressure value, but above a "semi-liquid food" standard maximum pressure value, and if the time for the volume of food to flow through the band was in a given range, then the patient chewed the food bolus well, as shown in FIG. 11A. On the other hand, if the pressure-time data gathered show a maximum pressure higher than the standard maximum pressure value and if the food flow time took longer, then the bite of food was not chewed well, as shown in FIG. 11C. In the latter case, the patient may be given a signal in a visual, graphical, auditory, written or tactile form that the bite was not chewed enough. In case the excessive pressure exceeds certain values and/or its duration is too long, the system will open the emergency pressure relief valve and the patient will be advised through his/her personal display to visit his/her physician for band readjustment (see "Automatic gastric pressure relief" below).

In another example, when the pressure sensor senses that the present bolus still passes through the band and a second peak of pressure is sensed prior to the stoma orifice emptying, then the system will indicate to the patient that he/she is eating to fast and he/she should slow down.

To emphasize—the information provided to the patient through his/her personal display provides the patient with insight of what happens inside his/her abdomen. It paces and trains the patient to slow down the speed of eating, informs the patient about the quality of chewing and provides the patient with positive results when achieved and negative ones if not. As the patient gets visual information regarding the size of the meal, he/she can consume until personal caloric or volume limits are met. The patient can adjust the portions taken to his/her new visually induced estimates. All these changes in patient's eating behavior will assist him/her to adopt a more suitable eating behavior in response to the new physical condition created by the AGB or any other bariatric procedures, instead of having to do it "blindly", as done in common practice now.

Further examples of possible recommendations for the patient and indications for the health caregiver for behavior changes may include (but not be limited to) the following:

1. Pacing patient's food processing and consumption
2. Time to eat.
3. Food passage busy—stop
4. Food passage clear—go
5. Pace the food processing
6. Pace the food intake
7. Bite chewed less then required 8. No drinking during meal
9. Caloric intake too high
10. End of meal,
11. Stop eating system clogged
12. Visit your surgeon time for inspection
13. Visit your surgeon—band empty
14. Visit your surgeon—suspected problem detected For the caregiver/physician:
1) Patient eats liquid food or suspected complication
2) Patient eats too fast
3) Patients eats too much
4) Patient does not chew his food enough
5) Patient eats/drinks high caloric food/liquid
6) Patients vomits too often
7) Possible complication—erosion, band leakage, port detachment
8) Possible complication—band slippage, pouch enlargement
9) Band deflated due to occlusion
10) New calibration required Automatic Gastric Pressure Relief FIG. 12 describes a method of relieving pressure in the gastric band using the relief emergency mechanism. In step 1202, the pressure sensor provides pressure vs. time data. In step 1204, the measured pressure P is checked against a factory set maximum pressure $P_{max}$. If P is equal to or greater than $P_{max}$, the relief valve is automatically opened in step 1206, discharging excessive saline into the abdomen or into the reservoir, thereby releasing the pressure inside the AGB. This leads to a larger stoma orifice, allowing clearance of occlusion into the stoma, thus avoiding ischemia, erosion or necrotic processes in the respective organ. If the measured P is smaller than $P_{max}$, then it is in the allowed pressure zone and further processing takes place. Optionally, in step 1208, P is checked against a pressure $P_{setmax}$ set by the physician. If P is equal to or greater than $P_{setmax}$, the relief valve is automatically opened in step 1210, discharging excessive saline into the abdomen or into the reservoir, thereby releasing the pressure inside the AGB. If the measured P is smaller than $Pset_{max}$, then it is in the allowed pressure zone and further processing takes place. Further optionally, in step 1212, both P and a time of measurement t are checked against a minimal pressure set by the physician $P_{setmin}$, and a time maximum set by the physician $t_{setmax}$. If P is equal to or greater than $P_{setmin}$ or if t is equal to or greater than $t_{setmax}$, the relief valve is automatically opened in step 1214, discharging excessive saline into the abdomen or into the reservoir, thereby releasing the pressure inside the AGB. If both are smaller than the set values, then nothing is done and the measurements continue. After each pressure relief in either of steps 1206, 1210 or 1214, the patient is instructed in step 1216 to see the physician for recalibrations of the gastric band.

Controlled Delivery of a Substance

Figure 13:
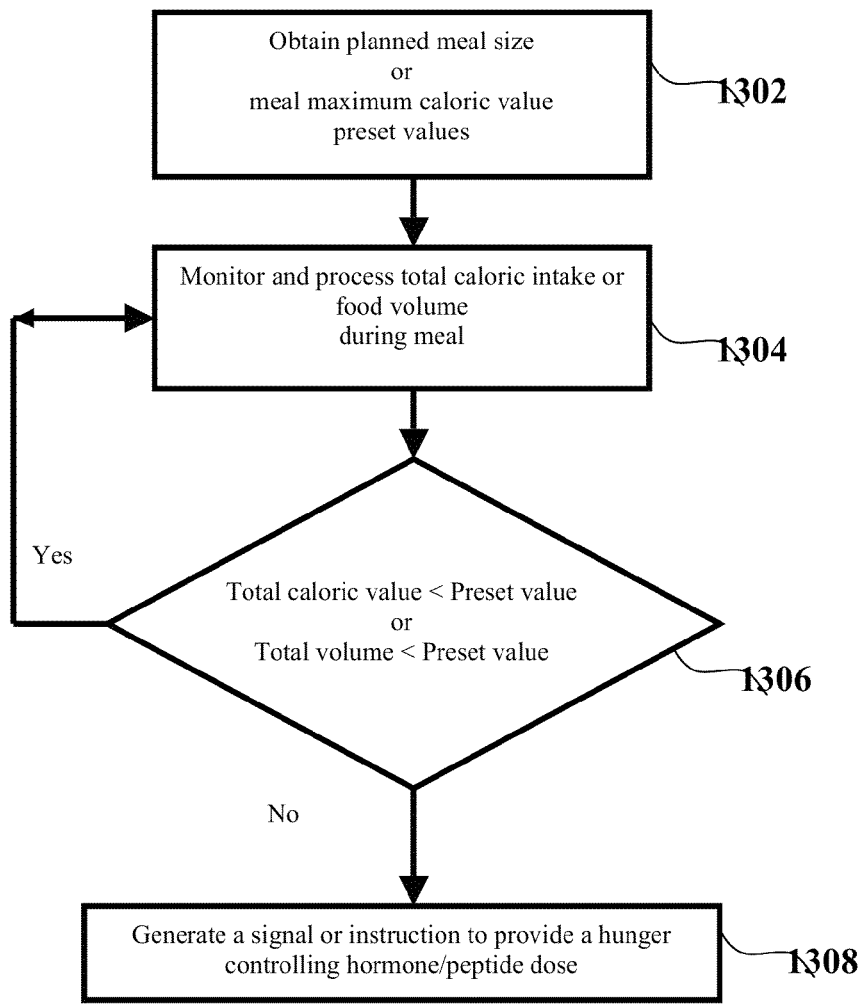
FIG. 13 describes a method of controlling automatic administration of a hunger controlling hormone or peptide.

FIG. 13 describes a method of controlling automatic administration of a hunger controlling hormone or peptide. Here, an apparatus of the invention is used to provide an input which can be converted into an instruction to the patient to activate an infusion pump to deliver a dose of the substance. The signal generation will depend on a preset caloric level the patient is allowed to consume in that meal. In step 1302, a specify meal size either by mass or by caloric values is provided as "preset" values. In step 1304, the food ingested is monitored and the total caloric intake and other parameters are obtained using any of the apparatuses of the invention. In step 1306, the total caloric intake and/or the total actual consumption volume is compared with the preset values. If either measured value exceeds the respective preset value, In case actual consumption reach to preset values, a signal is generated or an instruction is provided to an infusion pump to provide a hunger controlling hormone/peptide such as PYY36 dose in step 1308. If the measured value does not exceed a preset value, the monitoring continues.

The various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein. In addition, citation or identification of any reference in this application shall not be construed as an admission that such reference is available as prior art to the invention.

Although the descriptive data collected for each bolus and for each meal provides valuable information for the care giver and the patient and can be used to guide the patient. The incorporation of this data into a continuous follow-up report that presents the evolution of the eating behaviors along a period of time or following an event of band readjustment. The re-adjustment of the band is considered by some physicians as a "reparation with a new stoma size and a new pressure regime at the band pouch interaction", hence by providing a descriptive chart of the changes in the various parameter and behavior following each re-adjustment, we are providing the care giver with very important clinical tool that can help him to make clinical decisions and advise the patient of how to his change eating behaviors Out of the numerous possibilities to interpret and manipulate eating behavior collected data and patterns, integration of the various parameters and charts into valuable clinical descriptive information, FIG. 14A-F (as one possible example) describes one of the possible ways to process the collected data as indicated below. It is to be clearly understood that other data may be represented to patient or physician for further notes and investigation. Note: although the measured parameter is volume we can assume the consumed food staff is of a specific gravity of 1 or close to it and represent the results as volume in cc or weight in gr as sometimes presented below. We can make this assumption as the calculated value be it volume or weight is important as a reference point for a certain eating behavior. The significant information is the change from the base value.

FIG. 14A-F provides a non limiting example of some possible descriptive charts deduced from the measured data that are related to eating behavior patterns of a certain patient.

Patient_____John_____Doe_____Hospital_____TAMC Date_____Feb. 19, 2009_

Adjustment No.5 Patient Initial BMI43 Patient current BMI 35.5

Figure 14A:
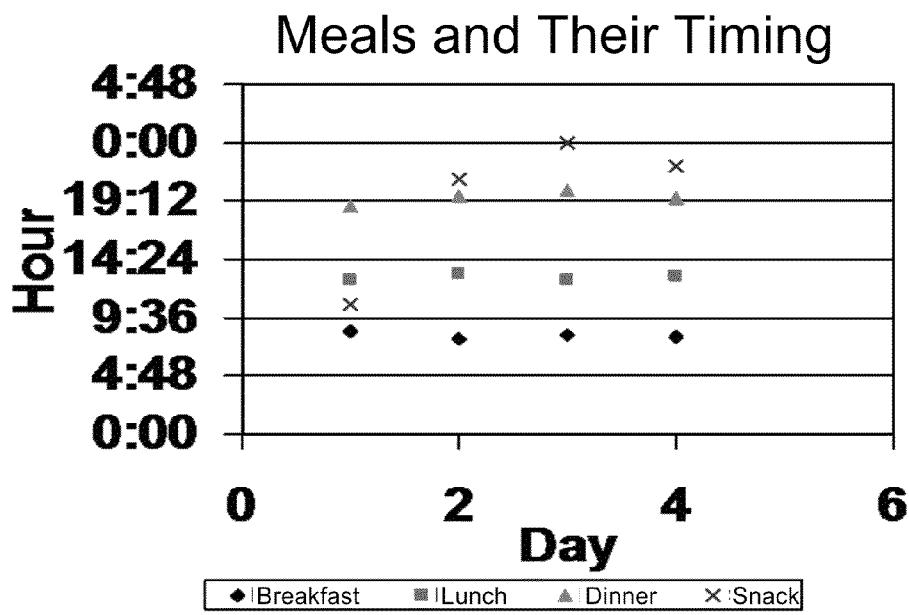
FIG. 14A-F provides a non limiting example of some possible descriptive charts deduced from the measured data that are related to eating behavior patterns.
Figure 14B:
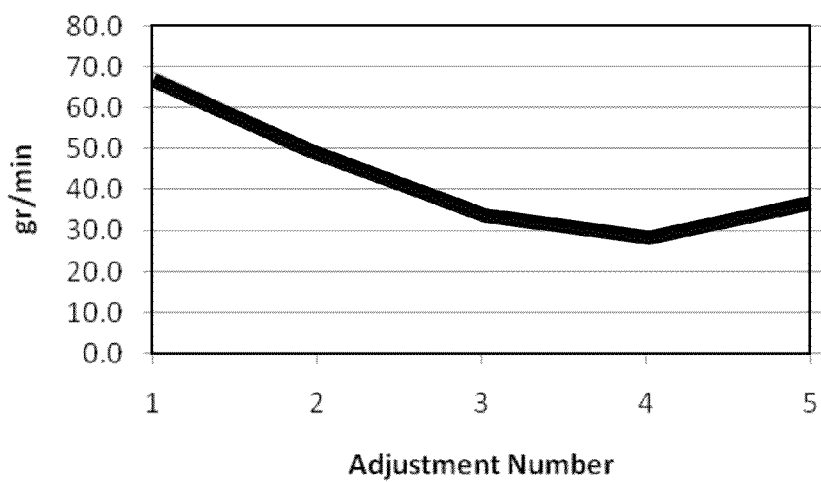
Figure 14C:
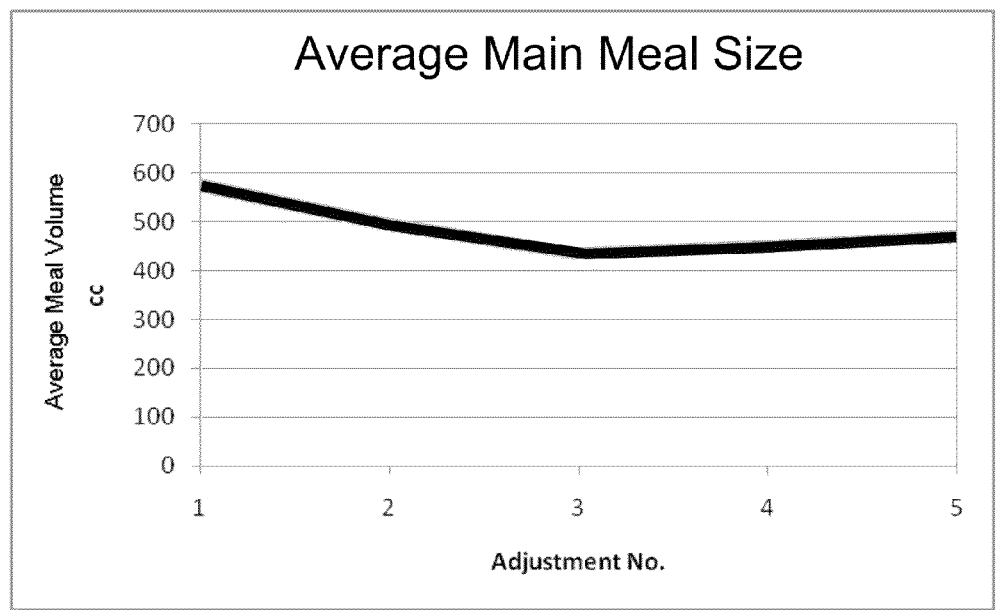

| Parameter | Data | Remarks |
|---|---|---|
| Patient's BMI | Increased from 34.2 kg/m2 to 35.5 kg/m2 | Check changes in eating parameters |
| Number of meals/day and their times | Reference is made to FIG. 14A which illustrates a patient which had 3 main meals & 1 snack meals/day at irregular hours, and late at night | Advise patient to adopt more regular hours and stop night eating. |
| Main meals eating rate Eating rate of main meals increased from last visit from 29.7 gr/min to 38.1 | see FIG. 14B | Advise patient to slow down eating and increase intervals between bites. Check consumed food type meal size and duration And advise proper changes. |
| Average main meal size Average meal size increased from 460 gr to 480 gr per meal | see FIG. 14C | A minor increase in meal size should check meal duration, if shorter advise patient to slow down and reduce volume |
| Average main meal duration The average main meal duration decreased from 15.5 minutes to 12.6 minutes | see FIG. 14D | Meal duration decreased advise patient to increase the duration by better chewing the food and by increasing intervals between bites. |
| Patient food tolerance The patient is suffering from 1-2 vomiting episodes per main meal. Although the number of events decreased from 7 to 5 the frequency is very high. | See FIG. 14E | Advise patient: To improve chewing, to increase the intervals between bites, if feels fullness in upper abdomen to stop eating. Advise patient against self induced vomiting. |
| Type & volume of consumed food The total daily consumed volume decreased marginally from 2300 cc/day to 2250 cc/day. There was a 29% shift from solid food to liquid food. | see FIG. 14F | Advise patient to move back to solid food, improve chewing and increase intervals between bites. Ask patient about caloric content of liquid/semi liquid foods. Advise patient against shifting to liquid or semi liquid food. |
| Please note: | BMI increased since last adjustment, speed of eating and meal size as well, 29% of the consumed solid food shifted to liquid food and the number of vomiting events decreased. Patient may have shifted to liquid or semi liquid high caloric food. | Advise patient against the consumption of high caloric liquid or semi liquid food |

Integrating a clock, (available on any microcontroller or microprocessor operated system) into the sensed element of bolus passage, by any possible sensing element, one can determine the time of the day in which a bolus had passed the stoma.

In this way, it is possible to map every bolus, type of bolus (liquid, semiliquid, solid) and daily occurrence. Such mapping allows a physician, a dietician or a patient to trace meals, snacks liquid consumption. In order to change mapping into consumed volume, a 10 cc volume may be considered as a baseline for volume. Of course, each patient physician or other person can modify the volume factor by dividing a known volume of food, by the number of bolus required to consume the food. Hence the volumetric correcting factor for a specific patient may be determined, for liquid, semi liquid and solid food.

Out of this map, we can determine eating behavior, if a person is a constant speed eater, night eater, total size of meal, average volume of meal, and average time of meal. Volumetric consumption by time, as required to pace the meal, a map with smaller then recommended solid food occurrences may indicate Shifting to liquid food, food tolerance may be indicated as a bolus which does not pass the stoma, or vomit as high peak pressure of 2-5 sec.

FIG. 16A-F provides a non limiting example a method to generate some possible descriptive charts similar to FIG. 14 deduced from the measured data that are related to eating behavior patterns. By integrating the data collected and calculated according to the processes described in FIGS. 8, 9A, 9B, 10A, 10B and presenting various calculated relations between those parameters we can describe those relations in eating behavior terms along a period of time as shown in FIGS. 14A-F. As a non limiting example processes of certain relations we describe under FIGS. 16A-F some of the possible processes.

Figure 16:
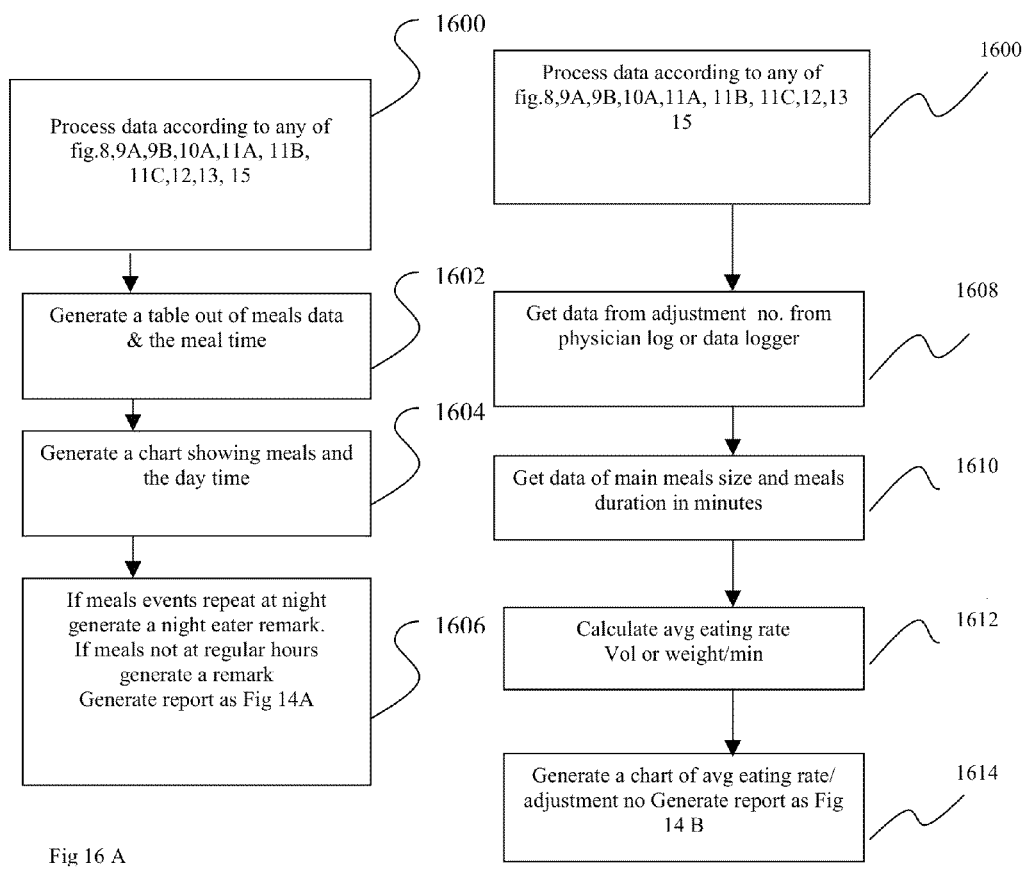
FIG. 16A-G provides a non limiting example a method to generate some possible descriptive charts deduced from the measured data that are related to eating behavior patterns.
Figure 16:
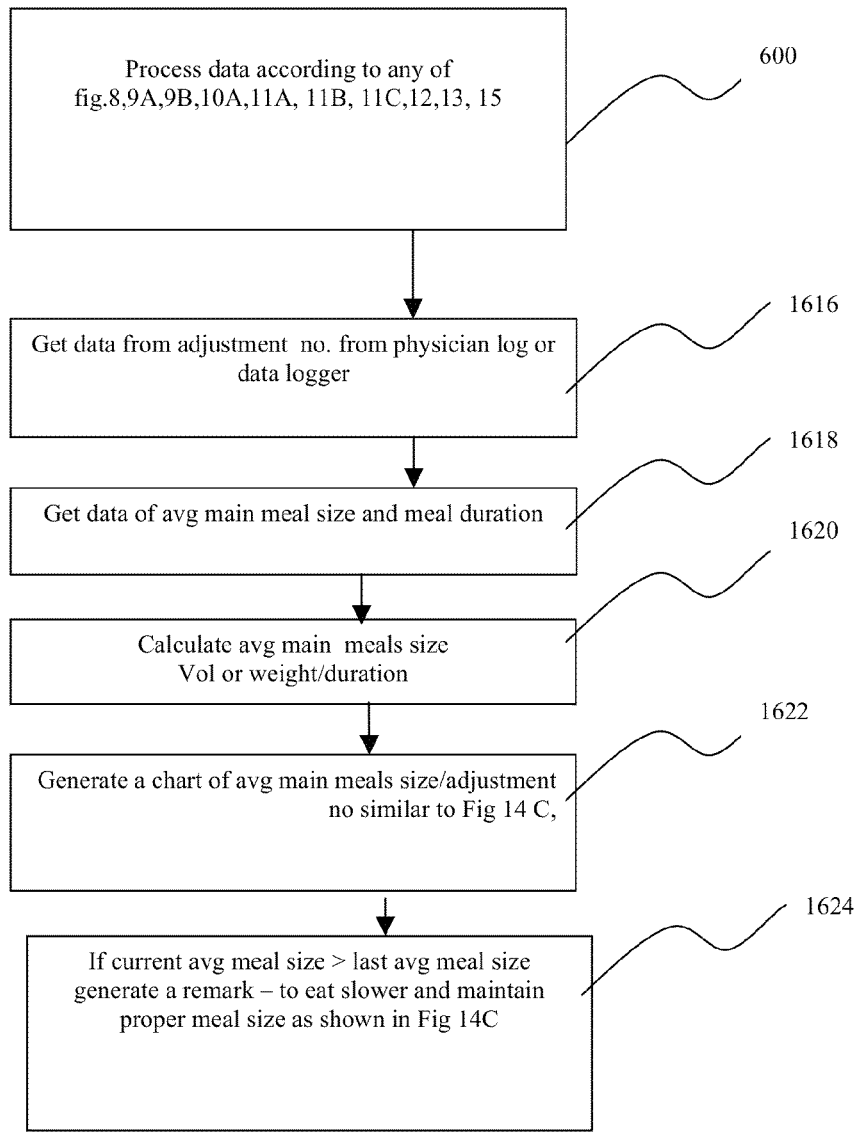
Figure 16:
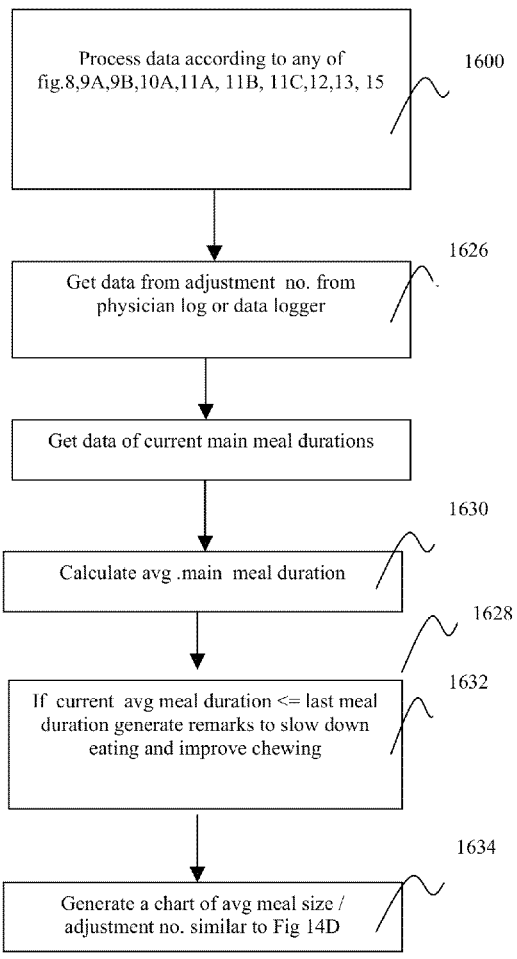
Figure 16:
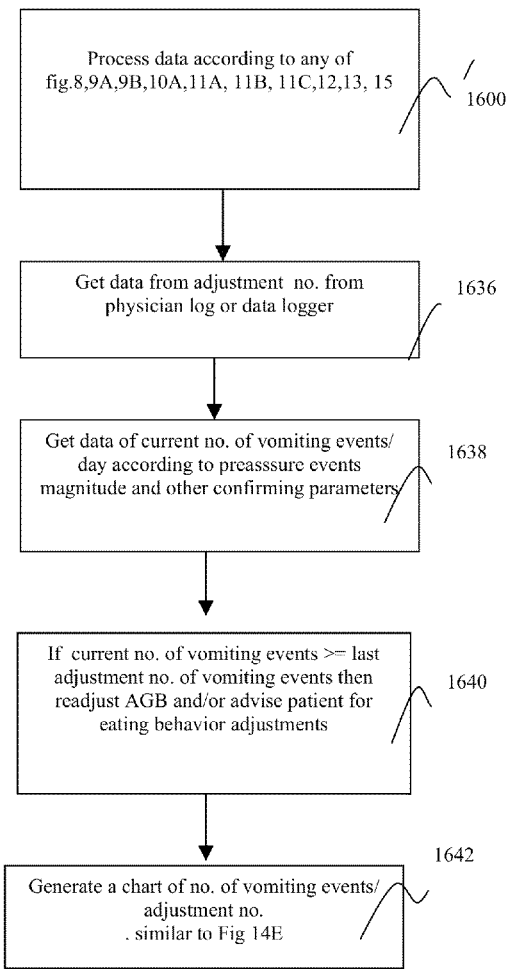

FIG. 16A illustrates the generation of the chart in FIG. 14A In step 1600 we process the data according to any of FIGS. 8, 9A, 9B, 10A, 11A, 11B, 11C, 12, 13, 15, in step 1602 we generate a table describing the number of meals per day and of the time of the day the meal took place, out this table we can then generate the chart FIG. 14A step 1604 that provides the care giver information of how regular are the meal times, the number of meals per day and if the patient eats at night. Based on this information we can generate remarks for the care giver or the patient to maintain regular eating times during the day and change the habit of night eating step 1606.

FIG. 16B illustrates the generation of the chart in FIG. 14B in step 1600 we process the data according to any of FIGS. 8, 9A, 9B, 10A, 11A, 11B, 11C, 12, 13, 15, In step 1608 we get from the data logger or from physician log the number of current re-adjustment of the band. In step 1610 we get data of main meals size by vol or weight and meals duration in minutes and then in step 1612 we calculate the average main meals eating rate in gr. or cc/min out of which we then generate the chart, step 1614, presenting avg. meal size after each re-adjustment event and a report as shown in FIG. 14B.

In the event of an increase in avg. meal size following the thightening of the band at readjustment a proper remark is generated for example, advise patient to slow down his eating rate, increase intervals between bites etc. and for the physician to evaluate if there might be a complication such as pouch enlargment or band errosion. FIG. 16C illustrates the generation of chart in FIG. 14C in step 1600 we process the data according to any of FIGS. 8, 9A, 9B, 10A, 11A, 11B, 11C, 12, 13, 15, In step 1616 we get from the data logger or from physician log the number of current re-adjustment of the band. In step 1618 and then in step 1620 we calculate the average main meals size in vol. or weight out of which we then generate the chart, step 1622, presenting avg. meal size after each re-adjustment event and a report step 1624 as shown in FIG. 14B. In the event of an increase in avg. meal size following the tightening of the band at readjustment a proper remark is generated for example, advise patient to slow down maintain recommended meal size and for the physician to evaluate if there might be a complication such as pouch enlargement or band erosion.

Figure 14D:
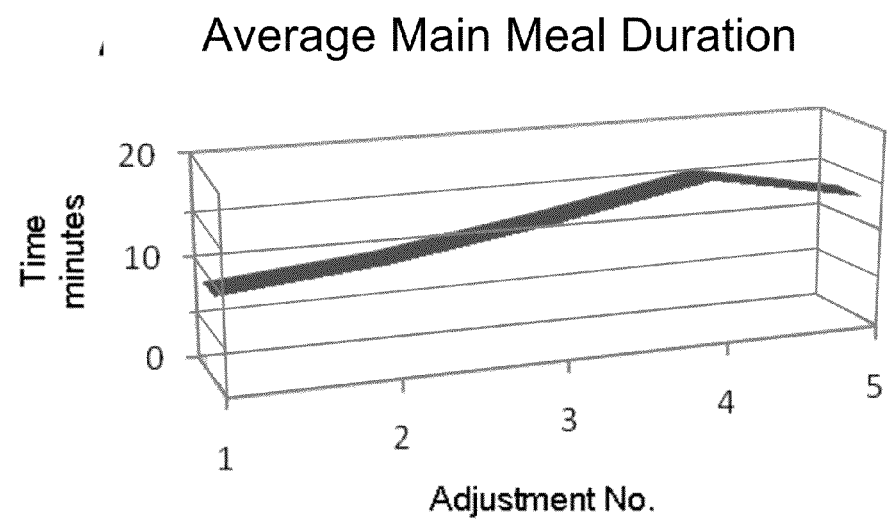

FIG. 16D illustrates the generation of chart in FIG. 14D in step 1600 we process the data according to any of FIGS. 8, 9A, 9B, 10A, 11A, 11B, 11C, 12, 13, 15, In step 1626 we get from the data logger or from physician log the number of current re-adjustment of the band. In step 1628 we get the data of main meals duration and in step 1630 we calculate the avg. main meals duration in step 1632 we compare the current avg. mail meals duration with the avg. main meals duration obtained after previous readjustment if the current avg. main meals duration<=previous avg. main meals duration then generate remarks to slow down and increase meals duration while maintaining recommended meal size, in step 1634 we generate a chart as shown in FIG. 14D.

Figure 14E:

FIG. 16E illustrates the generation of chart in FIG. 14E in step 1600 we process the data according to any of FIGS. 8, 9A, 9B, 10A, 11A, 11B, 11C, 12, 13, 15, In step 1636 we get from the data logger or from physician log the number of current re-adjustment of the band. In step 1638 we get the current number of vomiting events/main meals as determined by pressure magnitude, event duration and other validating parameters obtained from the various sensors. In step 1640 we compare the current number of events/meal with the number of vomiting events after the previous band readjustment if the current number>then previous number then generate a remark to physician to readjust the band and or suspect possible band slippage and a remark to advise the patient to slow eating rate and improve chewing of food. In step 1642 we generate out of this data a chart as presented on FIG. 14E.

Figure 14F:
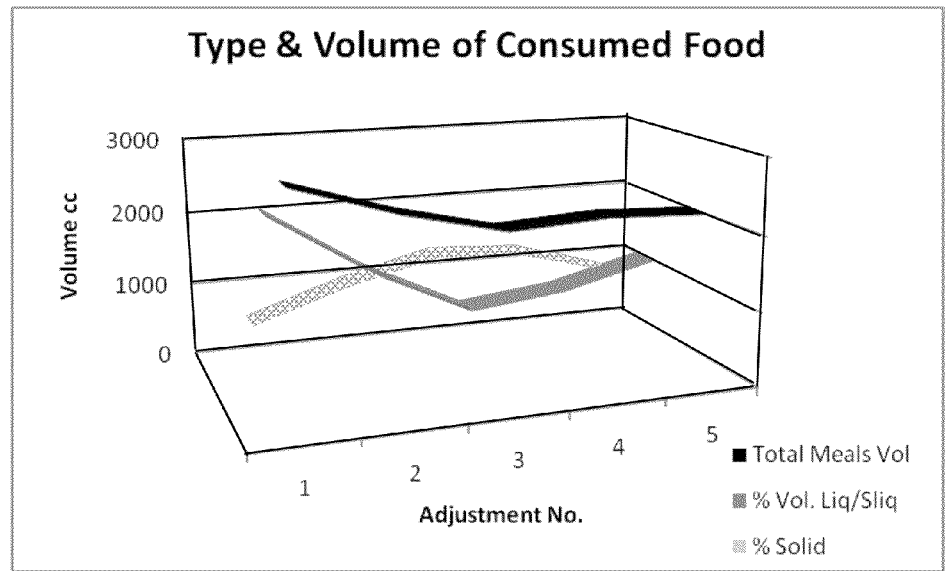
Figures 16F, 16G:
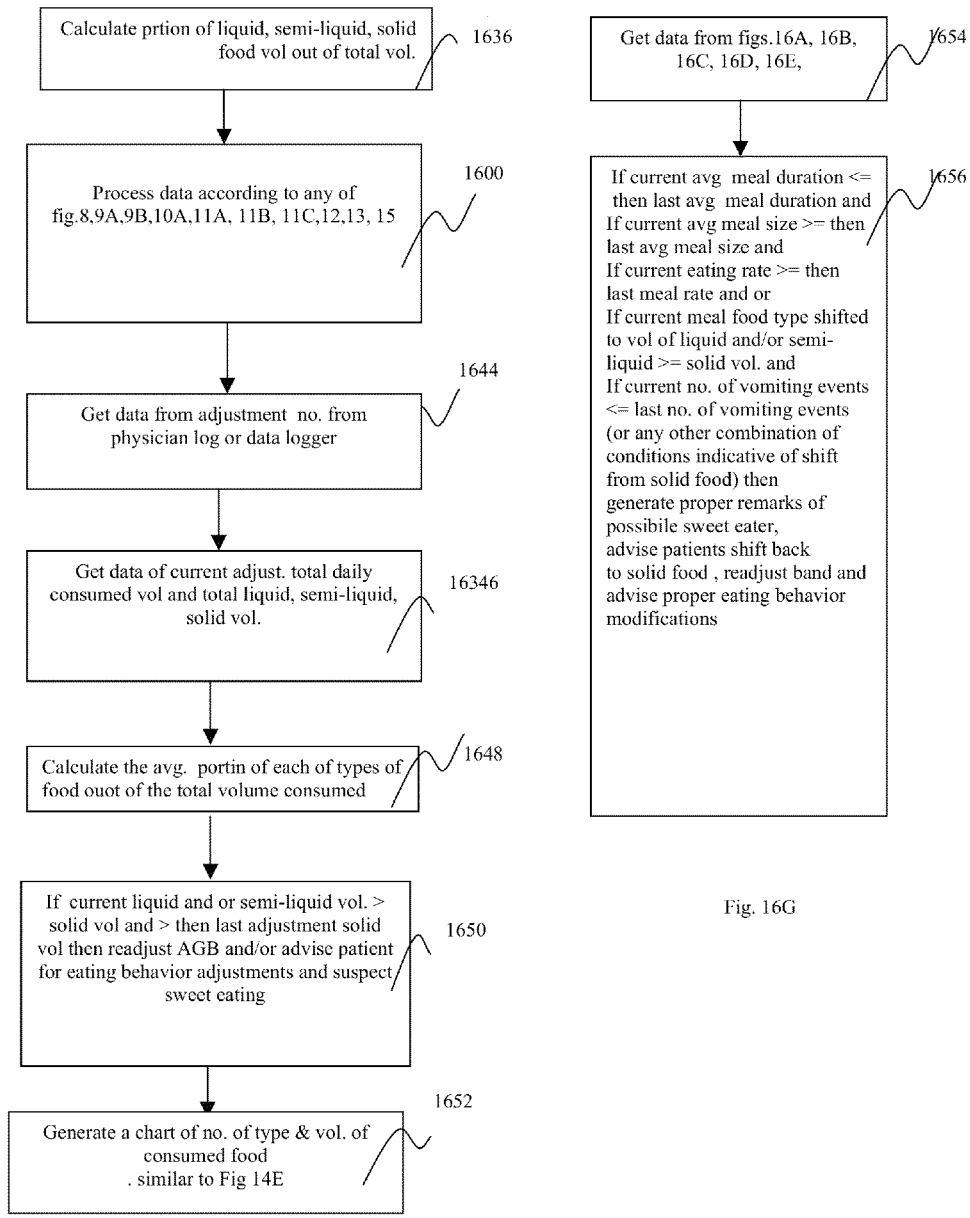

FIG. 16F illustrates the generation of chart in FIG. 14F in step 1600 we process the data according to any of FIGS. 8, 9A, 9B, 10A, 11A, 11B, 11C, 12, 13, 15, In step 1644 we get from the data logger or from physician log the number of current re-adjustment of the band. In step 1646 we get the current total volume or weight of food consumed during maim meals and the portion of the various types of food liquid, semi-liquid, solid out of the total. In step 1648 we compare the current avg. meal composition of each type of food with the same after previous band re-adjustment if the current food composition shifted from solid to liquid or semi-liquid as compared to the previous re-adjustment, if current liquid+semi liquid vol. or weight>=solid vol. or weight then generate a report step 1650 with remarks to advise patient to shift back solid food and evaluate the possible reasons and/or readjust band. Out of the data then generate a chart step 1652 as presented on FIG. 14G.

In FIG. 16G we get data step 1654 regarding the current parameters form FIGS. 16A, 16B, 16C, 16D, 16E, in step 1656 we compare the various parameters according to different relations such as presented hereunder and not limited to this example:

If current avg meal duration<=then last avg meal duration and If current avg meal size>=then last avg meal size and If current eating rate>=then last meal rate and or If current meal food type shifted to vol of liquid and/or semi-liquid>=solid vol. and If current no. of vomiting events<=last no. of vomiting events (or any other combination of conditions indicative of shift from solid food) then generate proper remarks of possible sweet eater, advise patients shift back to solid food, readjust band and advise proper eating behavior modifications, or similar instructions.

The invention claimed is:

1. A method for modifying eating behavior of a patient equipped with a gastric restriction apparatus (GRA), comprising the steps of:
   a) providing at least one external sensor in communication with a patient's hand;
   b) determining motion of said patient's hand by means of said external sensor;
   c) monitoring a parameter related to food currently passing through said GRA;
   d) increasing the signal received from said external sensor by filtering the influence of esophagus and lower esophagus sphincter (LES) so as to gather food passage events; and
   e) processing said parameter and said motion of said patient's hand, thereby providing an indication of a current eating pattern,
   wherein said steps of determining motion of said patients' hand and said step of providing an indication of a current eating pattern provides differentiation between at least two eating behavior patterns selected from a group consisting of: eating, vomiting, swallowing saliva, drinking directly from a glass, drinking via a straw, and eating liquid food with a spoon and any combination thereof.

2. The method according to claim 1, additionally comprising step of providing at least one second-type external sensor; further wherein said at least one second-type external sensor is selected from a group consisting of a vertical position sensor, thermometer, thermal sensor, force transducer, or a strain gauge, weighing, oscillating sensor for mass detection or any combination thereof.

3. The method according to claim 2, wherein said step (d) of increasing the signal received from said external sensor additionally comprises filtering the influence of patient posture while eating on food passage through the GRA.

4. The method according to claim 1, further comprising a step of using the indication of said current eating pattern to modify the eating behavior of said patient.

5. The method of claim 1, wherein said parameter related to food is pressure; further wherein said step of processing said parameter related to food is performed by determining at least one selected from a group consisting of volumetric flow, mass flow and Reynolds number.

6. The method of claim 1, further comprising a step of indicating current eating behavior through a display to the patient.

7. The method of claim 1, further comprising a step of calibrating the GRA to a desired restriction based on the monitored parameter.

8. The method of claim 1, further comprising at least one step selected from (a) monitoring said parameter on a standard food substance to obtain at least one standard food parameter; (b) comparing said monitored parameter to the at least one standard food parameter; or any combination thereof.

9. The method of claim 1, further comprising a step of indicating said eating behavior pattern to at least one selected from a group consisting of (a) said patient; (b) predetermined physician; or any combination thereof.

10. The method of claim 9, wherein said step of indicating is performed by at least one selected from a group consisting of (a) the patient; (b) said physician through appropriate instructions to the patient; or any combination thereof.

11. The method according to claim 1, additionally comprising a step of selecting said parameter from a group consisting of total size of meal, average volume of meal, average time of meal, volumetric consumption by time, shifting to liquid food consumption, vomiting events, type of food consumed, times of meals during the day, duration of meals, new adjustment validation data, short term change of pressure events as a result of new adjustment, long term change of pressure events as a result of new adjustment, and any combination thereof.

12. The method according to claim 1, wherein said step of processing said parameter and said motion of said patient's hand, thereby providing an indication of a current eating pattern comprises a step of indicating if said patient is at least one selected from a group consisting of a constant speed eater, a fast or accelerated speed eater, a night eater, a binge eater, and any combination thereof.

13. The method according to claim 1, wherein said external sensor is mounted in a position between the fingers and the elbow.

14. The method according to claim 1, wherein said external sensor is embodied in at least one element selected from a group consisting of a bracelet, hand watch belt, ring, elastic band wrapped around the arm, patch with one adhesive side, an add-on to a utensil, as an integral part of a utensil, and any combination thereof.

15. A method of modifying eating behavior of a patient equipped with a gastric restriction apparatus (GRA), comprising the steps of:
a) monitoring a parameter related to food currently passing through the GRA by means of at least one first-type external sensor;
b) increasing signal received from said at least one sensor by filtering the influence of esophagus and lower esophagus sphincter (LES) so as to gather food passage events; and
c) processing said parameter, thereby providing an indication of a current eating pattern, wherein said processing of said parameter is obtained according to a modification to the Navier-Stokes equation:
formula (a):

$$\rho\left(\frac{\partial v}{\partial t} + v \cdot \nabla v\right) = -\nabla p + \nabla \cdot \mathbb{T} + f,$$

where v is the flow velocity, ρ is the fluid density, p is the pressure. $\mathbb{T}$ is the deviatoric stress tensor, f represents body forces per unit volume acting on the fluid and $\nabla$ is the del operator; such that the following formula is used:
formula (b):

$$\frac{p_1 - p_2}{\rho} = \frac{1}{2}\left(\frac{16Q^2}{\pi^2 D_2^4} - \frac{16Q^2}{\pi^2 D_1^4}\right)$$

where $D_1$ is the pouch diameter, $D_2$ is stoma diameter, $P_1$ is upstream pressure, $P_2$ is downstream pressure, Q is the volumetric flow rate and p is upstream density thereby obtaining said parameter.

16. The method according to claim 15, additionally comprising step of providing at least one second-type external sensor; further wherein said at least one second-type external sensor is selected from a group consisting of a vertical position sensor, thermometer, thermal sensor, force transducer, or a strain gauge, weighing, oscillating sensor for mass detection or any combination thereof.

17. The method according to claim 15, further comprising a step of using the indication of said current eating pattern to modify the eating behavior of said patient.

18. The method according to claim 17, wherein said step (c) of increasing said signal received from said at least one sensor further comprises filtering the influence of patient posture while eating on food passage through the GRA.

19. The method of claim 15, wherein said step of providing an indication of said current eating pattern is performed through a display to the patient.

20. The method of claim 15, further comprising a step of calibrating the GRA to a desired restriction based on the monitored parameter.

21. The method of claim 15, further comprising at least one step selected from (a) monitoring said parameter on a standard food substance to obtain at least one standard food parameter; (b) comparing said monitored parameter to the at least one standard food parameter; or any combination thereof.

22. The method of claim 15, wherein said step of providing an indication of said current eating pattern is performed to at least one selected from a group consisting of (a) said patient; (b) predetermined physician; or any combination thereof.

23. The method of claim 22, wherein said step of providing an indication of said current eating pattern is performed by at least one selected from a group consisting of (a) the patient; (b) said physician through appropriate instructions to the patient; or any combination thereof.

24. The method according to claim 15, further comprising a step of selecting said parameter from a group consisting of total size of meal, average volume of meal, average time of meal, volumetric consumption by time, shifting to liquid food consumption, vomiting events, type of food consumed, times of meals during the day, duration of meals, new adjustment validation data, short term change of pressure events as a result of new adjustment, long term change of pressure events as a result of new adjustment, and any combination thereof.

25. The method according to claim 15, wherein said step of providing further comprises a step of indicating if said patient is at least one selected from a group consisting of a constant speed eater, a fast or accelerated speed eater, a night eater, a binge eater, and any combination thereof.

26. The method according to claim 15, wherein said at least one first-type-external sensor is mounted in a position between the fingers and the elbow.

27. The method according to claim 15, wherein said at least one first-type external sensor is embodied in at least one element selected from a group consisting of a bracelet, hand watch belt, ring, elastic band wrapped around the arm, patch with one adhesive side, an add-on to a utensil, as an integral part of a utensil, and any combination thereof.

* * * * *